US008560075B2

(12) United States Patent
Covalin

(10) Patent No.: US 8,560,075 B2
(45) Date of Patent: Oct. 15, 2013

(54) APPARATUS AND METHOD FOR THE TREATMENT OF HEADACHE

(76) Inventor: Alejandro Covalin, Los Angeles, CA (US)

( * ) Notice: Subject to any disclaimer, the term of this patent is extended or adjusted under 35 U.S.C. 154(b) by 236 days.

(21) Appl. No.: 12/578,369

(22) Filed: Oct. 13, 2009

(65) Prior Publication Data

US 2010/0030299 A1  Feb. 4, 2010

Related U.S. Application Data

(63) Continuation of application No. PCT/US2008/060288, filed on Apr. 14, 2008.

(60) Provisional application No. 60/911,518, filed on Apr. 13, 2007.

(51) Int. Cl.
*A61N 1/00* (2006.01)

(52) U.S. Cl.
USPC ............................ 607/46; 607/139; 600/13

(58) Field of Classification Search
USPC ...................................... 607/46, 139; 600/13
See application file for complete search history.

(56) References Cited

U.S. PATENT DOCUMENTS

| 397,474 | A | * | 2/1889 | Stanley ........................ 607/148 |
| 3,850,161 | A | | 11/1974 | Liss |
| 3,902,502 | A | | 9/1975 | Liss et al. |
| 4,550,733 | A | | 11/1985 | Liss et al. |
| 4,559,948 | A | | 12/1985 | Liss et al. |
| 4,574,808 | A | | 3/1986 | Liss et al. |
| 4,583,547 | A | * | 4/1986 | Granek et al. ................. 600/388 |
| 4,586,509 | A | | 5/1986 | Liss et al. |
| 4,614,193 | A | | 9/1986 | Liss et al. |
| 4,627,438 | A | | 12/1986 | Liss et al. |
| 4,784,142 | A | | 11/1988 | Liss et al. |
| 4,803,988 | A | * | 2/1989 | Thomson ........................ 607/70 |
| 4,813,418 | A | | 3/1989 | Harris |

(Continued)

FOREIGN PATENT DOCUMENTS

| EP | 06 74 5813 | 4/2010 |
| EP | 08 74 5813 | 4/2010 |
| JP | 08 173551 | 7/1996 |

OTHER PUBLICATIONS

Clarke et al, Transcranial magnetic stimulation for migraine: clinical effects, 2006, J. Headache Pain, 7, 341-346.*

(Continued)

*Primary Examiner* — Niketa Patel
*Assistant Examiner* — William Levicky
(74) *Attorney, Agent, or Firm* — Charles A. Lemaire; Lemaire Patent Law Firm, P.L.L.C.

(57) ABSTRACT

A battery-operated transcutaneous electrical nerve stimulator (TENS) to treat headache pain in an abortive and/or preventive manner. The TENS unit and its electrodes are built into a unitary device which facilitates a self-administered treatment. In some embodiments, the pulses are monophasic. In other embodiments, pairs of biphasic pulses are provided, wherein each pair of biphasic pulses includes a first pulse having a first polarity separated by a gap in time from a second pulsed having an opposite polarity. In some embodiments, each pulse in each biphasic pair is of a duration equal to that of the other pulse of the pair. In some embodiments, the duration of each pulse is between about 50 microseconds and about 400 microseconds, and the gap in time between pulses of a pair is between about 50 and 100 microseconds.

28 Claims, 22 Drawing Sheets

(56) References Cited

U.S. PATENT DOCUMENTS

| | | | |
|---|---|---|---|
| 4,844,075 A | | 7/1989 | Liss et al. |
| 4,856,526 A | | 8/1989 | Liss et al. |
| 4,997,418 A | * | 3/1991 | DeMartini .................. 604/20 |
| 5,078,928 A | | 1/1992 | Balster et al. |
| 5,109,847 A | | 5/1992 | Liss et al. |
| 5,117,826 A | | 6/1992 | Bartelt et al. |
| 5,421,817 A | | 6/1995 | Liss et al. |
| 5,449,378 A | | 9/1995 | Schouenborg |
| 5,851,223 A | | 12/1998 | Liss et al. |
| 6,023,642 A | * | 2/2000 | Shealy et al. .................. 607/74 |
| 6,132,392 A | * | 10/2000 | Stone .............................. 601/21 |
| 6,532,379 B2 | | 3/2003 | Stratbucker |
| 6,735,475 B1 | | 5/2004 | Whitehurst et al. |
| 7,012,797 B1 | * | 3/2006 | Delida .......................... 361/230 |
| 2005/0102006 A1 | * | 5/2005 | Whitehurst et al. ............ 607/46 |
| 2005/0278001 A1 | * | 12/2005 | Qin et al. ........................ 607/48 |
| 2006/0173510 A1 | | 8/2006 | Besio et al. |
| 2006/0195146 A1 | | 8/2006 | Tracey et al. |
| 2006/0206163 A1 | | 9/2006 | Wahlstrand et al. |
| 2007/0232966 A1 | | 10/2007 | Applebaum et al. |
| 2008/0014011 A1 | | 1/2008 | Rossen |
| 2009/0105738 A1 | | 4/2009 | Apperson et al. |
| 2009/0308888 A1 | | 12/2009 | Dairaku et al. |

OTHER PUBLICATIONS

PCT Prelim Report on Patentability for related app. PCTUS0860288 IPRP, Oct. 20, 2009.

Ahmed, H.E., et al., "Use of Percutaneous Electrical Nerve Stimulation (PENS) in the Short-term Management of Headache", "Headache", Apr. 2000, pp. 311-315, vol. 40.

WIPO Search Report for priority app. PCT/US08/60288 S.R., Sep. 8, 2008.

Bartsch, et al., "Stimulation of the greater occipital nerve induces increased central excitability of dural afferent input", 2002, pp. 1496-1509., vol. Brain, No. 125.

Buchgreitz, et al., "Increased prevalence of tension-type headache over a 12-year period is related to increased pain sensitivity. A populati", "Cephalalgia", 2007, pp. 145-152, vol. 27.

Carolei, et al., "Comorbidities of migraine: a user-friendly overview", "The Journal of Headache and Pain", 2003, pp. s23-s25, vol. 4.

Dartigues, et al., "Evaluating the economic costs of migraine: interest of a comparative approach", 2003, pp. s63-s66, vol. 4, Publisher: The Journal of Headache and Pain.

Iannazzo, et al., "Analgesic therapy for headache: consumption, appropriateness and costs", "The Journal of Headache and Pain", 2003, pp. s84-s87, vol. 4.

Jensen, R., "Mechanisms of tension-type headache", "Cephalalgia", 2001, pp. 786-789, vol. 21.

Jensen, R., "Peripheral and central mechanisms in tension-type headache: an update", "Cephalalgia", 2003, pp. 49-52, vol. 23 Suppl 1.

Lipton, et al., "The global burden of migraine", "The Journal of Headache and Pain", 2003, pp. s3-s11, vol. 4.

Martelletti, et al., "The global impact of migraine", "The Journal of Headache and Pain", 2003, pp. s1-s2, vol. 4.

Mork, et al., "Possible mechanisms of pain perception in patients with episodic tension-type headache. A new experimental model of myof", "Cephalalgia", 2004, pp. 466-475, vol. 24.

Popeney, et al., "Peripheral neurostimulation for the treatment of chronic, disabling transformed migraine", "Headache", 2003, pp. 369-375, vol. 43.

Rodrigo-Royo, et al., "Peripheral Neurostimulation in the Management of Cervicogenic Headache: Four Case Reports", "Neuromodulation", 2005, pp. 241-248, vol. 8.

Schwedt, et al., "Response to occipital nerve block is not useful in predicting efficacy of occipital nerve stimulation", "Cephalalgia", 2007, pp. 271-274, vol. 27.

Texas Instruments, "Using the TPS61040 in High-Voltage Applications", "Texas Instruments applications report SLVA209", May 2005.

Solomon, et al., "Migraine-cluster headache syndrome", "Headache", 1985, pp. 236-239, vol. 25.

Stovner, et al., "The global burden of headache: a documentation of headache prevalence and disability worldwide", "Cephalalgia", 2007, pp. 193-210, vol. 27.

Terzi, et al., "Greater occipital nerve blockade in migraine, tension-type headache and cervicogenic headache", "The Journal of Headache and Pain", 2002, pp. 137-141, vol. 3.

Vinding, et al., "The burden of headache in a patient population from a specialized headache centre", "Cephalalgia", 2007, pp. 263-270, vol. 27.

PCT Search Report for related app. PCT/US12/37666 S.R.

* cited by examiner

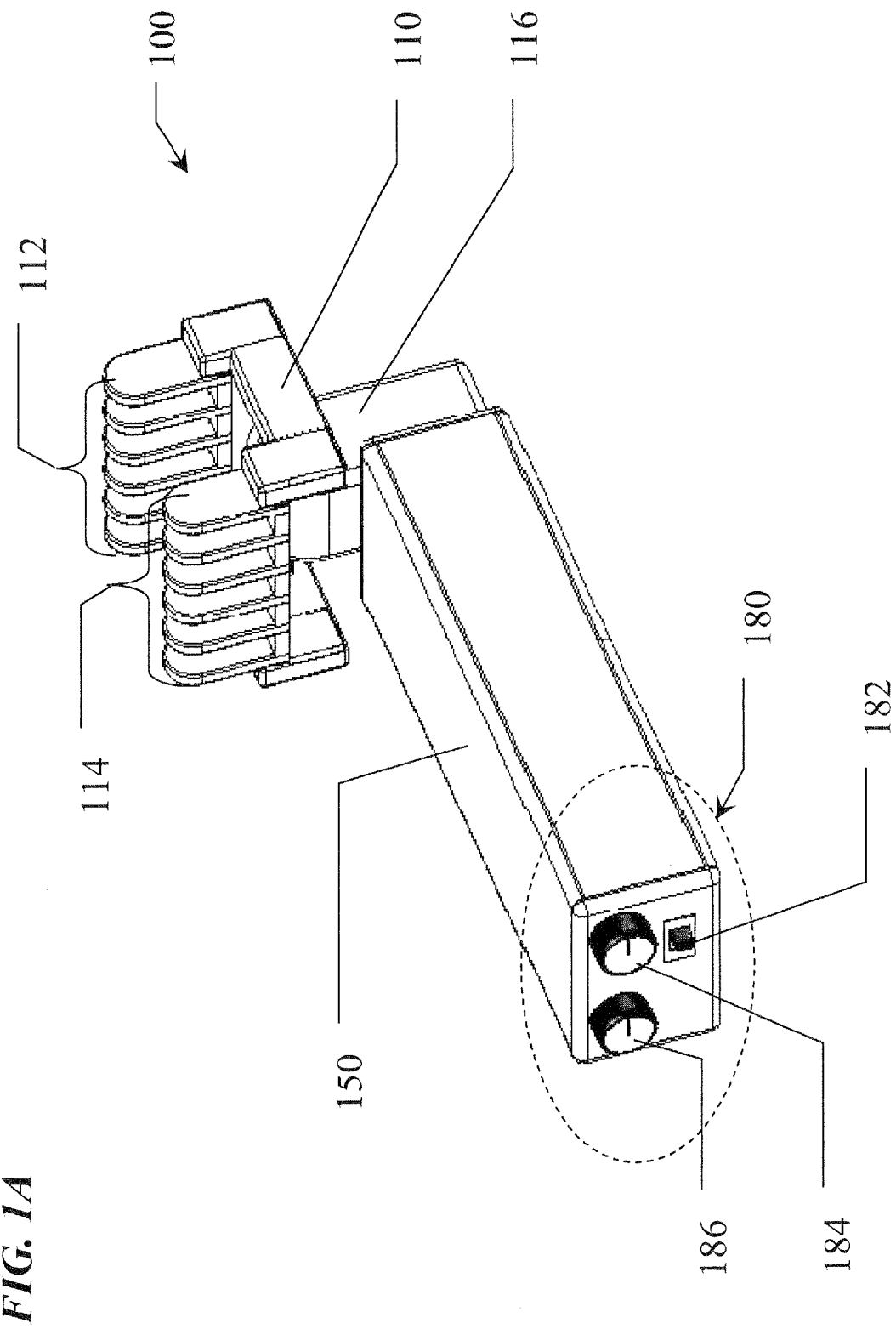

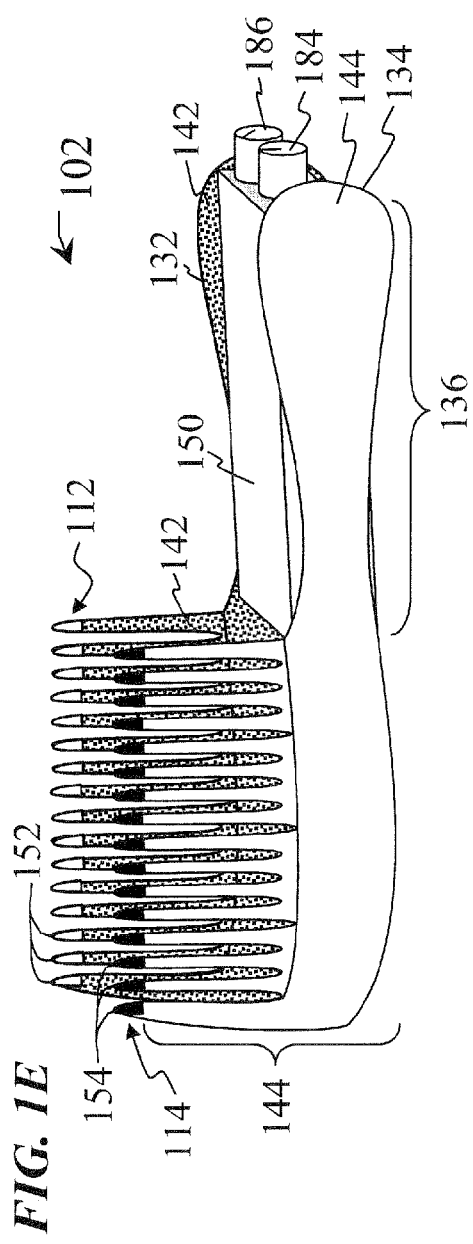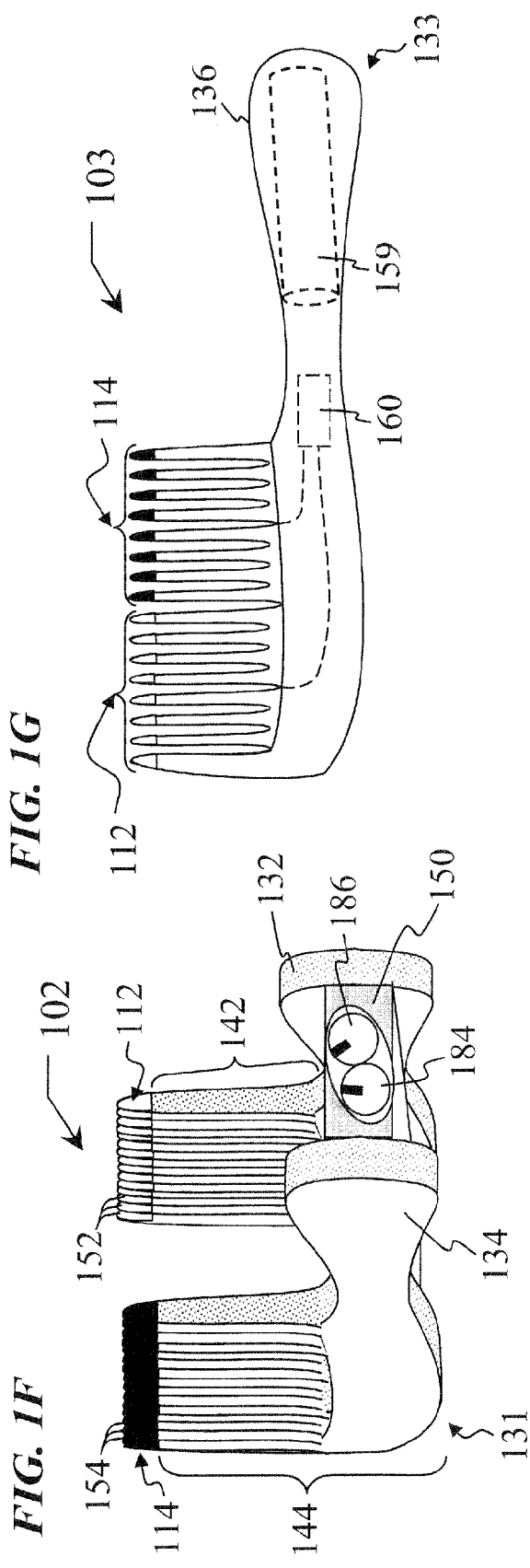

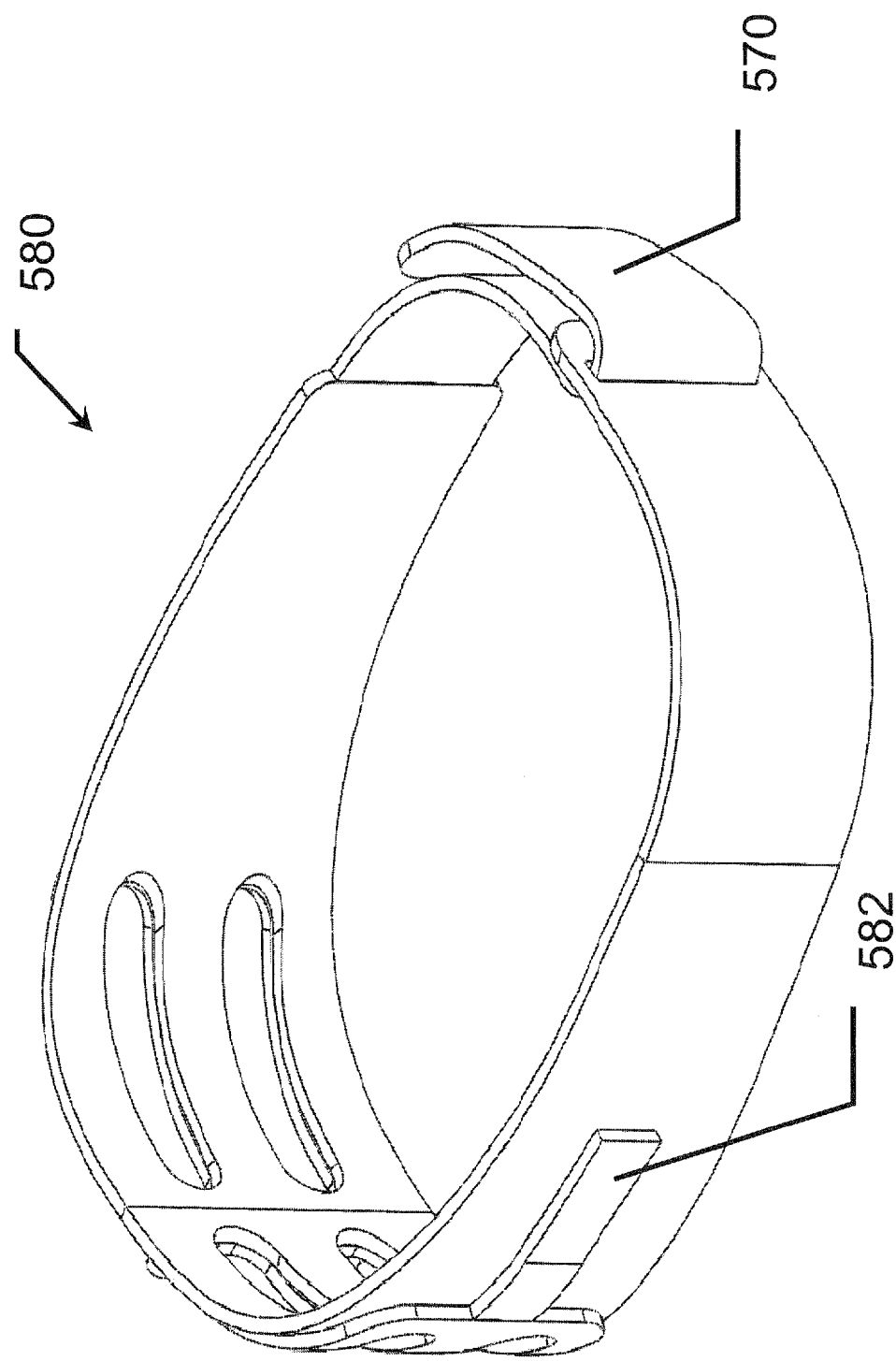

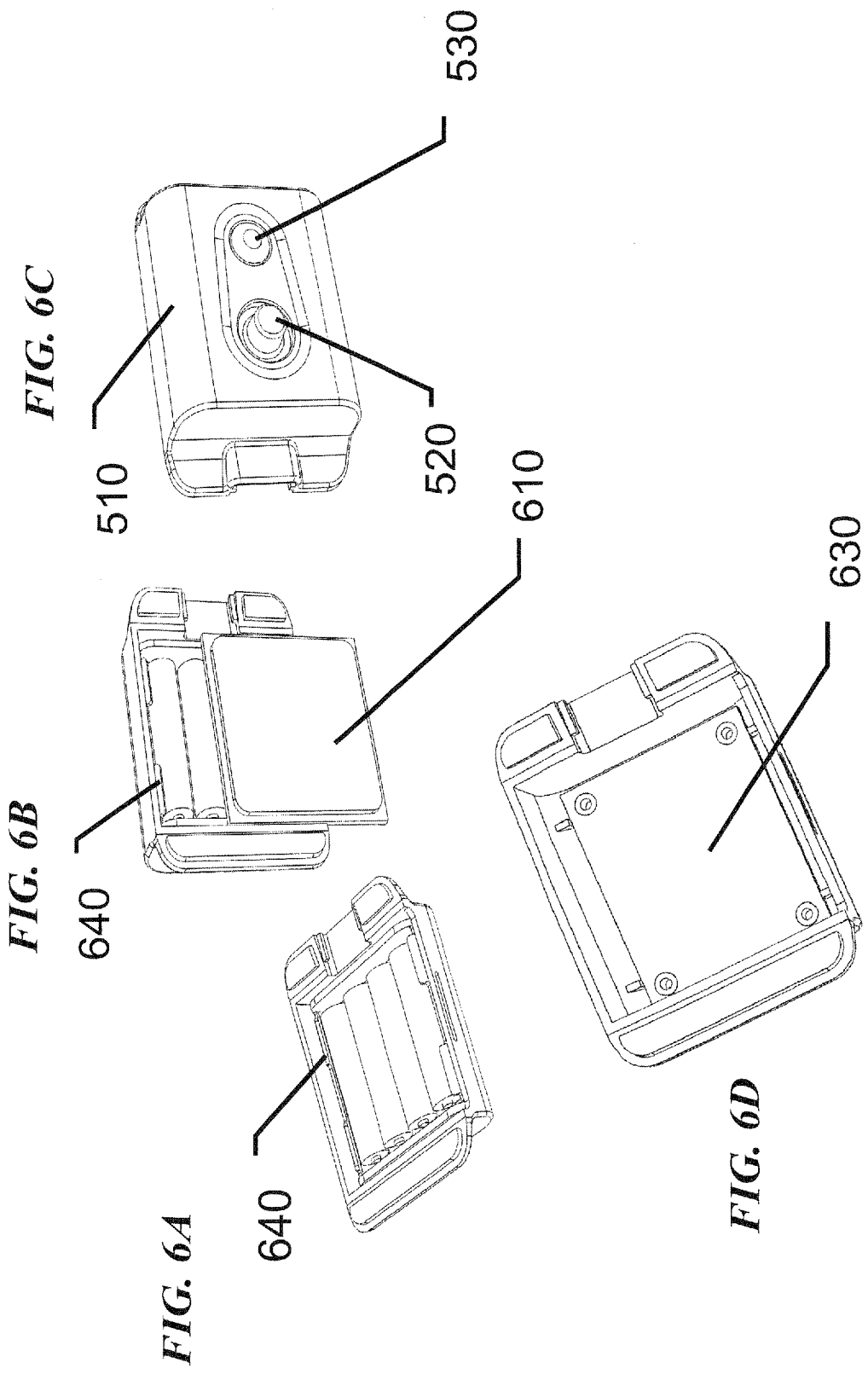

SPACED BIPHASIC

ALTERNATING
SPACED BIPHASIC

ALTERNATING
UNSPACED BIPHASIC

MONOPHASIC

SPACED BIPHASIC
WITH PLURAL SUBPULSES

APPARATUS AND METHOD FOR THE TREATMENT OF HEADACHE

CROSS-REFERENCE TO RELATED APPLICATIONS

This application is a continuation of International Patent Application No. PCT/US2008/060288, with an international filing date of Apr. 14, 2008 (International Publication No. WO 2008/128215, with a publication date of Oct. 23, 2008), which claimed priority to U.S. Provisional Patent Application No. 60/911,518 filed Apr. 13, 2007, titled "APPARATUS AND METHOD FOR THE TREATMENT OF HEADACHE," each of which is incorporated herein by reference in its entirety.

FIELD OF THE INVENTION

This invention relates to methods and apparatus for the treatment of headache and more specifically to a method and a portable, (e.g., battery-operated) transcutaneous electrical stimulation device for the treatment of headache.

BACKGROUND OF THE INVENTION

Headache is so common that it is often not regarded as a serious health issue. However, more than 45 million Americans suffer from headaches sever enough to seek medical help.

A study published in the April 1999 issue of the Archives of Internal Medicine revealed that one single headache type, namely migraine, costs American employers $13 billion per year due to missed work and reduced productivity. In addition, according to the National Headache Foundation (NHF), approximately 157 million workdays are lost annually due to the pain and the associated symptoms of migraine. On top of the above mentioned economic impact, there are intangible costs, such the poor quality of life of these headache sufferers due to the time missed from their daily activities.

The International Headache Society (IHS) classifies headache disorders into two main categories: primary and secondary. The main difference between these two categories is that the secondary type headaches are attributed to a particular cause. The twelve headache types within both categories are listed below in Table 1 and a more in detailed comparison of the first three primary headaches can be found in Table 2.

TABLE 1

International classification of headache disorders

Primary Headaches

1. Migraine
2. Tension-type headache (TTH)
3. Cluster headache
4. Other primary headaches Secondary Headaches 5. Headache attributed to head and/or neck trauma
6. Headache attributed to cranial or cervical vascular disorder
7. Headache attributed to non-vascular intracranial disorder
8. Headache attributed to a substance or its withdrawal
9. Headache attributed to infection
10. Headache attributed to disorder of homeostasis
11. Headache or facial pain attributed to disorder of cranium, neck, eyes, ears, nose, sinuses, teeth, mouth or other facial or cranial structures
12. Headache attributed to psychiatric disorder

TABLE 2

Characteristics of Primary Headache Disorders

|  | Migraine | Tension-Type Headache (TTH) | Cluster Headache |
| --- | --- | --- | --- |
| Location | Unilateral | Bilateral | Strictly unilateral |
| Intensity | Moderate/severe | Mild/moderate | Severe |
| Duration | 4 to 72 hours | Episodic: 30 min to 7 days | 15 to 90 min |
| Sufferers in the U.S. | 29.5 million | 78% of adult population | One million |

Although the overall mechanisms and specific pathways responsible for primary and secondary headaches are still being elucidated, it is well known that many patients that experience these types of headaches often feel pain in both the front and the back of the head. While the front of the head is innervated, among others, by the ophthalmic branch of the trigeminal nerve, the back of the head is mainly innervated by spinal branches arising from C1 through C4, which are the first four cervical spinal nerves and which, among others, form the occipital and suboccipital nerves. However, recent studies suggest that there is a functional connection between the branches of the nervous system that innervate the front and the back of the head.

The most commonly used treatment to mitigate headache pain is to date the pharmacological approach, which, depending on the particular drug, according to the American Council for Headache Education and to the National Guideline Clearinghouse (NGC) has various potential side effects. Some of these side effects include: fatigue, depression, nausea, insomnia, weight gain, constipation, dizziness, low blood pressure, gastrointestinal irritation, impaired platelet function, renal complications, analgesic rebound headache, and hepatic complications.

Studies exploring alternative treatments for headaches have shown that electrically stimulating spinal nerve branches arising from between C1 through C4 provide an effective technique to mitigate several types of headaches. Electrostimulation of other sites in the head has also been successfully used to treat headaches. A study by Solomon et al. used high frequency (12 kHz to 20 kHz) electrostimulation in which one electrode was placed over the area of maximum pain and a second electrode on the opposite side of the head. In the same study, in cases where the pain was generalized, one electrode was placed in the occiput (back of the head) and another on the right hand. Solomon found that fifty-five percent (55%) of patients perceived an improvement a few minutes after the onset of the electrostimulation.

In another study by Ahmed et al., percutaneous electrical nerve stimulation (PENS) was used to treat tension-type headache (TTH), migraine and posttraumatic headache (PTH); this study revealed that, regardless of the type of headache, pain was significantly mitigated; 58%, 58% and 52% in TTH, migraine, and PSH respectively. On top of the pain reduction, a reduction in the frequency of headaches was also observed.

As mentioned above, electrostimulation of the spinal branches arising from C1 through C4 in the occipital and suboccipital region has proven to be effective in mitigating pain and reducing the frequency of occurrence of several types of headaches. However, the approach taken involves the chronic implantation of electrodes into the aforementioned anatomical region along with the implantation of a stimulating unit (sometimes referred to as an implantable pulse generator (IPG)), in a second location or in the same region (see U.S. Pat. No. 6,735,475, which is incorporated herein by reference) to produce the stimulating signal. Several scientific publications assess the effectiveness of this approach (e.g., Manjit et al., 2004; Popeney and Alo, 2003; Schwedt, et al., 2007a; Schwedt, et al., 2007b; Rodrigo-Royo et al., 2005).

U.S. Pat. No. 4,856,526 and U.S. Pat. No. 4,627,438 to Liss et al., which are incorporated herein by reference, describe the approach by Solomon, which includes electrodes fixed to the head, with the inconvenience that cables running from the electrodes to the stimulation unit (pulse generator) are needed. In addition, fixing the electrodes, which are disposable, in place requires the use of non-permanent biocompatible conductive glue.

In the PENS approach, needles have to protrude and penetrate the skin in specific locations and at specific depths, which renders a self treating paradigm nearly impossible. In addition, the PENS approach requires a skilled and well trained person to position the needles. On top of that, cables need to be used to connect the needles to the stimulator unit and the needles are disposable (typically not reusable, or they must be sterilized between uses, adding expense to the use of the PENS approach).

As stated above, although chronic implantation of a stimulator unit and electrodes to treat headaches mitigates pain and disability in most patients, it has the caveat that the patient must undergo a surgical procedure and be left with at least one foreign body chronically implanted. This approach might be acceptable for and by a subpopulation of patients with severe and quasi permanent debilitating headaches; however, the majority of those suffering from debilitating headaches suffer them on average once a month.

Other non-specific approaches such as the one suggested in U.S. Patent Application Publication Number U.S. 2006/0173510 (which is incorporated herein by reference), also has the inconvenience that electrodes have to be fixed and cables have to be used to connect the electrodes to the stimulating unit.

U.S. Pat. No. 5,078,928 (hereinafter, "Balster et al."), titled "COATING PROCESS FOR MANUFACTURING ENLARGED SMOOTH TEETH ENDS ON COMB", issued Jan. 7, 1992, describes a process that could be used to manufacture smooth, comb-like electrodes, and is incorporated herein by reference. Balster et al. describe a process for permanently attaching smooth-finished globules of coating material to the ends of the teeth of molded plastic combs, picks, lifts and the like, including roughening or oxidizing the teeth ends to remove the gloss finish and form a more adherent surface; dipping the roughened teeth ends into a bath of liquid coating material to attach a globule of coating material to each tooth end and cover the sharp mold-parting line located thereat; and drying the globules attached to the teeth ends.

Clearly, the majority of the patient population suffering from headaches would benefit from, and what is needed are a self-contained (i.e., one piece with no interconnecting cables and/or wires) portable device and a side-effect-free (e.g., non-pharmaceutical) yet effective non-invasive treatment method that could be self administered via the self-contained portable device that can be used in both preventative and abortive ways. This invention discloses such a device and method.

BRIEF SUMMARY OF THE INVENTION

The invention herein disclosed describes a non invasive apparatus and method for the acute treatment of primary and secondary type headaches via transcutaneous electrostimulation of the spinal nerve branches and/or sub branches and/or any of their combinations such as those arising from C1 through C4, including, but not limited to, the right and/or left suboccipital nerve(s), the right and/or left greater occipital nerve(s), the right and/or left least (third) occipital nerve(s), the right and/or left lesser occipital nerve(s), the right and/or left great auricular nerve(s).

In some embodiments, the apparatus includes a device where the stimulating electrodes and the stimulator are integrated into a single handheld battery-operated transcutaneous electrical nerve stimulating (TENS) device. The aforementioned TENS device can be, but does not have to be, operated by the patient himself or herself.

In some embodiments, the apparatus includes a device where the stimulating electrodes and the stimulator are integrated into a single hands-free battery-operated transcutaneous electrical nerve stimulating (TENS) device. In some such embodiments, the patient is free to move and his/her hands are free to do other tasks while the stimulation is being applied. The aforementioned TENS device can be, but does not have to be, operated by the patient himself or herself.

In some embodiments, the apparatus includes a device where the stimulating electrodes and the stimulator are integrated into a single handheld battery-operated transcutaneous electrical nerve stimulating (TENS) device, which can be worn on the hand and/or wrist of the patient. In some such embodiments, the electrodes are located at the tip of the fingers on a glove-like garment which extends toward the wrist where the control box is strapped in a fashion similar to how a wrist watch is strapped.

In some embodiments, the stimulation is applied by making contact between the electrodes and the area of the head where the above-mentioned nerves are located. Once the electrodes are correctly positioned, the TENS device or the electrodes are moved (by moving the hand of the person administering the therapy) without losing contact between the electrodes and the body, so that electrical stimulation is applied to the area and its surroundings.

In some embodiments, the stimulation is applied by securing the entire device to the head of the patient (rendering a hands-free, free-to-move operation) making contact between the electrodes and the area of the head where the above-mentioned nerves are located. In some such embodiments, since the patient is free to move and hands-free, he/she could be simultaneously performing many other regular tasks.

In some embodiments, in order to make stimulation more efficient, conductive gel is applied between the device and the treated area.

BRIEF DESCRIPTION OF THE DRAWINGS

FIG. 1A is a lateral-view perspective drawing of a TENS device 100.

FIG. 1E is a lateral-view perspective drawing of a TENS device 102 having a two-row comb-like structure.

FIG. 1F is a bottom-view perspective drawing of the TENS device 102 of FIG. 1E.

FIG. 1G is a lateral-view perspective drawing of a TENS device 103 having a single-sided comb-like structure.

FIG. 5E is an anterior drawing of the head-band 580.

FIG. 6 (composed of FIGS. 6A, 6B, 6C and 6D) are drawings of the control box.

DETAILED DESCRIPTION OF THE INVENTION

Figure 1B:
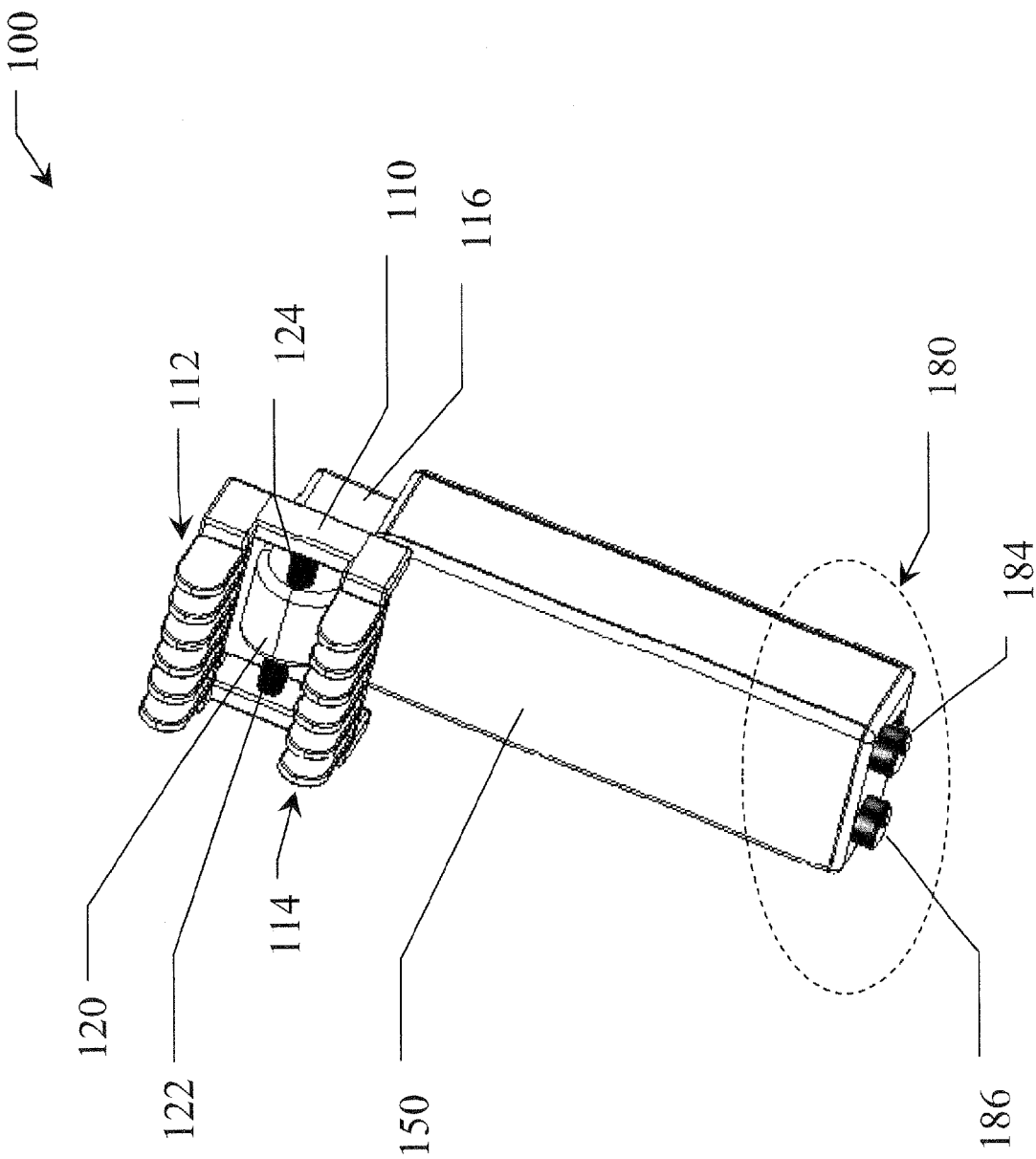
FIG. 1B is an anterior-view perspective drawing of TENS device 100.

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon the claimed invention.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures.

As stated in the background section, currently used devices and methods to treat headaches via electrostimulation are not ideal to treat the majority of the patient population suffering from headaches. In several of the cases, electrodes are flat, have to be fixed using adhesive, and connected via cables/wires to the pulse generator or electrostimulator. Furthermore, in some of these cases the electrodes are percutaneous needles which need to be placed by a well-trained person. In other cases, the patient needs to undergo surgery to be chronically implanted with the stimulating electrodes and their accompanying stimulating unit (sometimes referred to as an implantable pulse generator or IPG).

In contrast, one embodiment of the present invention provides a non-invasive handheld device with a plurality of protruding electrodes, which are suited to go through the hair of the patient, and additionally, the device can be used by a patient to self-administer treatment.

In another embodiment, the present invention provides a non-invasive hands-free device with one or more protruding electrodes, which are suited to go through the hair of the patient, and additionally, the device can be used by a patient to self-administer treatment.

In some embodiments, the present invention provides a transcutaneous electrical nerve stimulator (TENS) having a plurality of electrodes in which the stimulator and the plurality of electrodes are incorporated into a unitary device. As used herein, the term unitary device means a device having support for both the stimulator electronics and power supply and for the plurality of electrodes. For example, in some embodiments, a unitary device includes a comb-like device having a self-contained power supply (e.g., a battery) and electronics (e.g., the stimulator circuit) along with electrodes configured in one or more comb-like structures. In some such embodiments, the electrodes are manufactured according to method such as a modified version of the method of Balster et al. (U.S. Pat. No. 5,078,928, which is incorporated herein by reference), wherein the comb's teeth tips are coated with an electrically conductive smooth material such as conductive epoxy and/or are plated or otherwise coated with one or more metals such as nickel plated on a copper adhesion layer, and optionally coated with a hypoallergenic metal such as gold or platinum or the like. In some embodiments, a metal layer extends from the tips of some of the teeth (e.g., the half of the teeth at a distal end of the comb) to one or more contact points used to connect to the stimulator electronics, and another metal layer extends from the tips of others of the teeth (e.g., the half of the teeth at a proximate end of the comb) to one or more other contact points used to connect to the stimulator electronics. In other embodiments, a unitary device includes a headband-like device having a self-contained power supply (e.g., a battery) and electronics (e.g., the stimulator circuit) along with electrodes configured in one or more finger-like structures. In yet other embodiments, a unitary device includes a glove-like device having a self-contained power supply (e.g., a battery) and electronics (e.g., the stimulator circuit) along with electrodes configured in one or more protruding structures on the palm or fingers of the glove. In some embodiments, a unitary device does not use exposed or external wires. In some embodiments, a unitary device does not separate the power supply (e.g., a battery), electronics (e.g., the stimulator circuit), and electrodes into two or more separate sections connected to one another by wires or cables. In some embodiments, a unitary device facilitates a self-administered treatment by the patient.

In other embodiments, the present invention provides a transcutaneous electrical nerve stimulator (TENS) having a plurality of electrodes in which the stimulator and the plurality of electrodes are incorporated into a multi-portion device with the portions connected to one another by cables, wires, or the like. In some embodiments, separate devices are defined as two or more devices, wherein each device has their own separate support. For example, in some embodiments, the stimulator is connected to the plurality of electrodes via at least one electrical lead.

In some embodiments, each one of one plurality of electrodes (e.g., those electrodes in one ensemble of electrodes) is at least 0.1 millimeters apart from those of another plurality of electrodes (e.g., those electrodes in another ensemble of electrodes). In some embodiments, each one of first plurality of electrodes is at least 0.2 millimeters apart from all the electrodes in the second plurality of electrodes. In some embodiments, each one of the first plurality of electrodes is at least 0.5 millimeters apart from all the electrodes in the second plurality of electrodes. In some embodiments, each one of the first plurality of electrodes is at least 1 millimeter apart from all the electrodes in the second plurality of electrodes. In some embodiments, each one of the first plurality of electrodes is at least about 2 millimeters apart from all the electrodes in the second plurality of electrodes. In some embodiments, each one of the first plurality of electrodes is at least about 5 millimeters apart from all the electrodes in the second plurality of electrodes. In some embodiments, each one of the first plurality of electrodes is at least about 10 millimeters apart from all the electrodes in the second plurality of electrodes. In some embodiments, each one of the first plurality of electrodes is at least about 20 millimeters apart from all the electrodes in the second plurality of electrodes. In some embodiments, each one of the first plurality of electrodes is at least about 50 millimeters apart from all the electrodes in the second plurality of electrodes. In some embodiments, each one of the first plurality of electrodes is at least about 100 millimeters apart from all the electrodes in the second plurality of electrodes. In some embodiments, each one of the first plurality of electrodes is at least about 200 millimeters apart from all the electrodes in the second plurality of electrodes.

In some embodiments, the plurality of electrodes is configured such that at least two electrodes touch a patient's skin simultaneously. In some embodiments, the plurality of electrodes is configured such that at least three electrodes touch a patient's skin simultaneously. In some embodiments, the plurality of electrodes is configured such that at least four electrodes touch a patient's skin simultaneously. In some embodiments, the plurality of electrodes is configured such that at least five electrodes touch a patient's skin simultaneously. In some embodiments, the plurality of electrodes is configured such that at least six electrodes touch a patient's skin simultaneously. In some embodiments, the plurality of electrodes is configured such that at least seven electrodes touch a patient's skin simultaneously. In some embodiments, the plurality of electrodes is configured such that at least eight electrodes touch a patient's skin simultaneously. In some embodiments, the plurality of electrodes is configured such that at least nine electrodes touch a patient's skin simultaneously. In some embodiments, the plurality of electrodes is configured such that at least ten electrodes touch a patient's skin simultaneously. In some embodiments, the plurality of electrodes is configured such that at least fifteen electrodes touch a patient's skin simultaneously. In some embodiments, the plurality of electrodes is configured such that at least twenty electrodes touch a patient's skin simultaneously. In some embodiments, the plurality of electrodes is configured such that more than twenty electrodes touch a patient's skin simultaneously.

In some embodiments, the plurality of electrodes includes at least two electrodes. In some embodiments, the plurality of electrodes includes at least five electrodes. In some embodiments, the plurality of electrodes includes at least ten electrodes. In some embodiments, the plurality of electrodes includes at least twenty electrodes. In some embodiments, the plurality of electrodes includes more than twenty electrodes.

In some embodiments, each one of a plurality of electrodes has a cylindrical or comb-tooth shape. In some embodiments, each one of a plurality of electrodes has a pyramidal shape. In some embodiments, each one of a plurality of electrodes has a prism shape (e.g., polygonal or like shape in cross section and having a constant or tapered shape across a length of the prism). In some embodiments, each one of a plurality of electrodes has a cylindrical shape (e.g., cylindrical, oval or like shape in cross section and having a constant or tapered shape across a length of the tooth).

Having the electrodes protrude or extend to a length in the manner of the teeth of a comb facilitates placing or combing the electrodes through the hair so each one of a plurality of the electrodes reach the scalp or skin under the hair. In some embodiments, each one of the plurality of electrodes has a length and a cross-sectional diameter wherein the length is at least one-half times (0.5×) the cross-sectional diameter. In some embodiments, each one of a plurality of electrodes has a length and a cross-sectional diameter wherein the length is at least one times (1×) the cross-sectional diameter. In some embodiments, each one of a plurality of electrodes has a length and a cross-sectional diameter wherein the length is at least about two times (2×) greater than the cross-sectional diameter. In some embodiments, each one of a plurality of electrodes has a length that is at least about three times (3×) greater than the cross-sectional diameter. In some embodiments, each one of a plurality of electrodes has a length that is at least about four times (4×) greater than the cross-sectional diameter. In some embodiments, each one of a plurality of electrodes has a length that is at least about five times (5×) greater than the cross-sectional diameter. In some embodiments, each one of a plurality of electrodes has a length that is at least about ten times (10×) greater than the cross-sectional diameter.

In some embodiments, each one of the plurality of electrodes has a length and a cross-sectional diameter wherein the length is about one-half times (0.5×) the cross-sectional diameter. In some embodiments, each one of a plurality of electrodes has a length and a cross-sectional diameter wherein the length is about one times (1×) the cross-sectional diameter. In some embodiments, each one of a plurality of electrodes has a length and a cross-sectional diameter wherein the length is about two times (2×) greater than the cross-sectional diameter. In some embodiments, each one of a plurality of electrodes has a length that is about three times (3×) greater than the cross-sectional diameter. In some embodiments, each one of a plurality of electrodes has a length that is about four times (4×) greater than the cross-sectional diameter. In some embodiments, each one of a plurality of electrodes has a length that is about five times (5×) greater than the cross-sectional diameter. In some embodiments, each one of a plurality of electrodes has a length that is about ten times (10×) greater than the cross-sectional diameter.

Figure 1C:
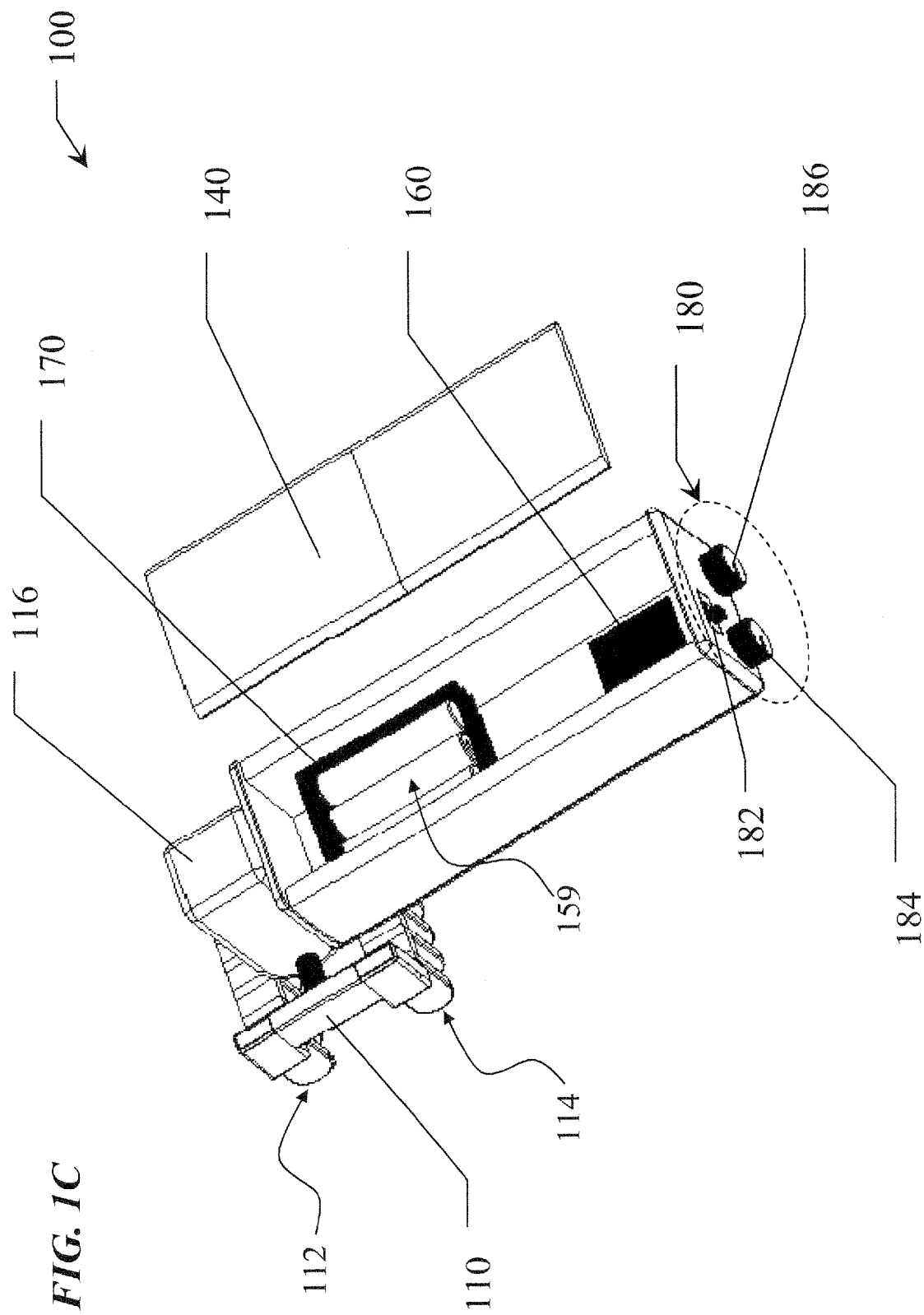
FIG. 1C is a posterior-view perspective drawing of TENS device 100 with its back lid 140 open.

FIG. 1A is a lateral-view perspective drawing of a handheld TENS device 100 (see FIGS. 1B and 1C for anterior and posterior views, respectively, of device 100). In some embodiments, device 100 includes a physically non-invasive transcutaneous electrical nerve stimulator (TENS) having one or more electrodes, in which the stimulator and the one or more electrodes are incorporated into a single, self-contained, handheld device 100 that is battery operated. In some embodiments, device 100 includes a handheld case 150, a top electrode ensemble 112, a bottom electrode ensemble 114, an electronic circuit 160, a battery holder 170, one or more batteries 159, and, in some embodiments, controls 180 including, e.g., an ON/OFF switch 182, a therapy selector knob 184, and an intensity selector knob 186.

Figure 1D:
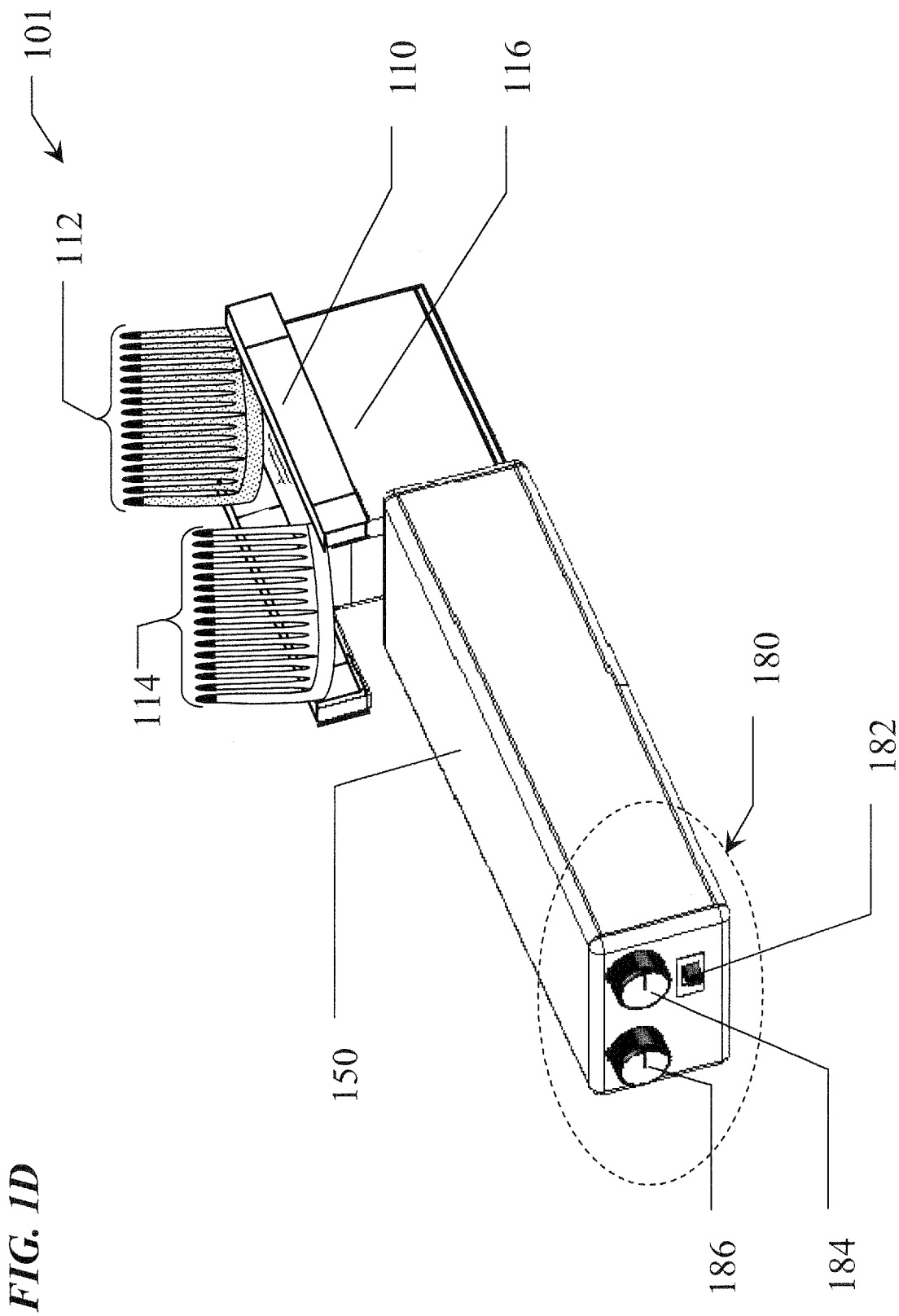
FIG. 1D is a lateral-view perspective drawing of a TENS device 101 having comb-like electrodes.

FIG. 1D is a lateral-view perspective drawing of a handheld TENS device 101 having electrode ensembles 112 and 114 implemented as comb-like teeth with conductive tips, wherein each conductive tooth top of electrode ensemble 112 is electrically connected to circuitry 160, e.g., by wires or a plated-metal layer (e.g., in some embodiments, a nickel plating on a vanadium or copper adhesion layer formed on the polymer comb structure, wherein, in some embodiments, the tips are then plated or otherwise coated with a hypoallergenic metal that is compatible with skin contact, such as gold or platinum, and wherein an insulating layer is then deposited over the metal layers except for the tips, which are left uninsulated so that they easily conduct electricity to the skin during therapy). In some embodiments, circuit 160 includes two output conductors, one of which is connected to the teeth of electrode ensemble 112, and the other of which is connected to the teeth of electrode ensemble 114.

FIG. 1E is a lateral-view perspective drawing of a TENS device 102 having a pair of spaced-apart rows of comb-like electrodes in rows or ensembles 112 and 114.

FIG. 1F is a bottom-view perspective drawing of the TENS device 102 of FIG. 1E. In some embodiments, a first comb-like structure 132 is metallized (or otherwise made of or coated with an electrically conductive material such as conductive epoxy), and then coated with in insulator (such as a polymer layer 142 leaving the conductive and/or metallized tips 152 exposed. Similarly, in some embodiments, a second comb-like structure 134 is metallized (or otherwise made of or coated with an electrically conductive material such as conductive epoxy), and then coated with in insulator (such as a polymer layer 144 leaving the conductive and/or metallized tips 154 exposed. In some embodiments, the enclosure 150 is sandwiched between comb-like structures 132 and 134, and electrically connected to a first electrode ensemble 112 and to a second electrode ensemble 114. In some embodiments, enclosure 150 holds an electronic circuit 160, a battery holder 170, one or more batteries 159 (such as shown in FIG. 1B), and, in some embodiments, presents one or more controls 180 including, e.g., an ON/OFF switch, a therapy selector knob 184, and an intensity selector knob 186. In some embodiments, electronics circuit 160 is electrically connected to first electrode ensemble 112 and second electrode ensemble 114 by electrical conductors (e.g., plated layers of metal or electrical wires, or conductive epoxy, which in some embodiments, are coated with an insulating layer such as a conformal polymer) within the dual-row comb-like structures 131.

FIG. 1G is a lateral-view perspective drawing of a TENS device 103 having a single-row comb-like structure 133, wherein first electrode ensemble 112 is formed from the teeth on the far end of the comb relative to the handle, and second electrode ensemble 114 is formed from the teeth on the end proximal to the handle 136. In some embodiments, the battery 159 and electronics circuit 160 (such as shown in FIG. 1B), are held within handle 136, and electronics circuit 160 is electrically connected to first electrode ensemble 112 and second electrode ensemble 114 by electrical conductors (e.g., plated layers of metal or electrical wires, or conductive epoxy) within the single-row comb-like structure 133.

Figure 12:
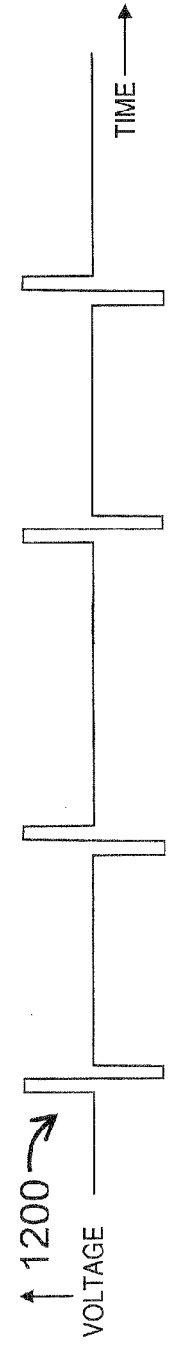
FIG. 12 is a diagram of an alternating unspaced biphasic pulse stream 1200.

In many cases, the muscle tissue of the patient is closer to the skin than are the nerves to which it is desired for the therapy device 100 to stimulate (this also applies to devices 101, 102, 103, 500, 900 or the like). Accordingly, in some embodiments, the pulses output from device 100 are made short enough to substantially avoid stimulating the muscles to contract while being long enough to stimulate the nerves (e.g., in some embodiments, each pulse of a plurality of pulses has a non-zero duration at most 400 microseconds, while in other embodiments, each pulse is at most 300 microseconds, each pulse is at most 250 microseconds, each pulse is at most 200 microseconds, each pulse is at most 150 microseconds, each pulse is at most 300 microseconds, each pulse is at most 100 microseconds, each pulse is at most 75 microseconds, or each pulse is at most 50 microseconds). Using such short pulses is generally sufficient to reduce or eliminate muscle stimulation, however, to then obtain successful nerve stimulation with the short pulses, the voltage and/or current of the pulses is increased. Further, in order to balance the charge injected into the nerves and tissue and to avoid skin irritation from charge imbalance, each pulse of one polarity is followed a short time later by a pulse of the opposite polarity (e.g., in some embodiments, a positive (or negative) pulse (e.g., with a pulse width (duration) of between about 50 microseconds and about 400 microseconds, in some embodiments) is transmitted, and after a short delay of, e.g., between about 50 microseconds and about 100 microseconds, a negative (or positive) pulse (e.g., with a pulse width (duration) of approximately the same duration as the positive pulse, in some embodiments) is transmitted. In some embodiments, the short delay between the two pulses of a pair of opposite-polarity pulses is thought to give the first pulse time to take effect before the charge-balancing second pulse is sent. In other embodiments, the charge-balancing second pulse is sent with no delay after the first pulse, such as shown in FIG. 12.

Figure 2:
FIG. 2 is a perspective drawing of the anatomy of the back of the head of a patient 99 showing different nervous structures.

In some embodiments, the present invention includes TENS device 100 (see FIG. 1A, FIG. 1B, and FIG. 1C), 101 (see FIG. 1D), 102 (see FIG. 1E and FIG. 1F), 103 (see FIG. 1G), 500 (see FIGS. 5A, 5B, 5C, 5D, 5E, 5F and FIGS. 6A, 6B, 6C, and 6D) and/or 900 (see FIG. 9) and methods for using the device to treat primary and secondary headache via transcutaneous (thus non-invasive) electrical stimulation of the spinal nerve branches and/or sub branches and/or any of their combinations arising from C1 through C4 (see FIG. 2), including, but not limited to, the right and/or left suboccipital nerve(s) 205, the right and/or left greater occipital nerve(s) 210, the right and/or left least (third) occipital nerve(s) 220, the right and/or left lesser occipital nerve(s) 230, the right and/or left great auricular nerve(s) 240.

Figure 5A:
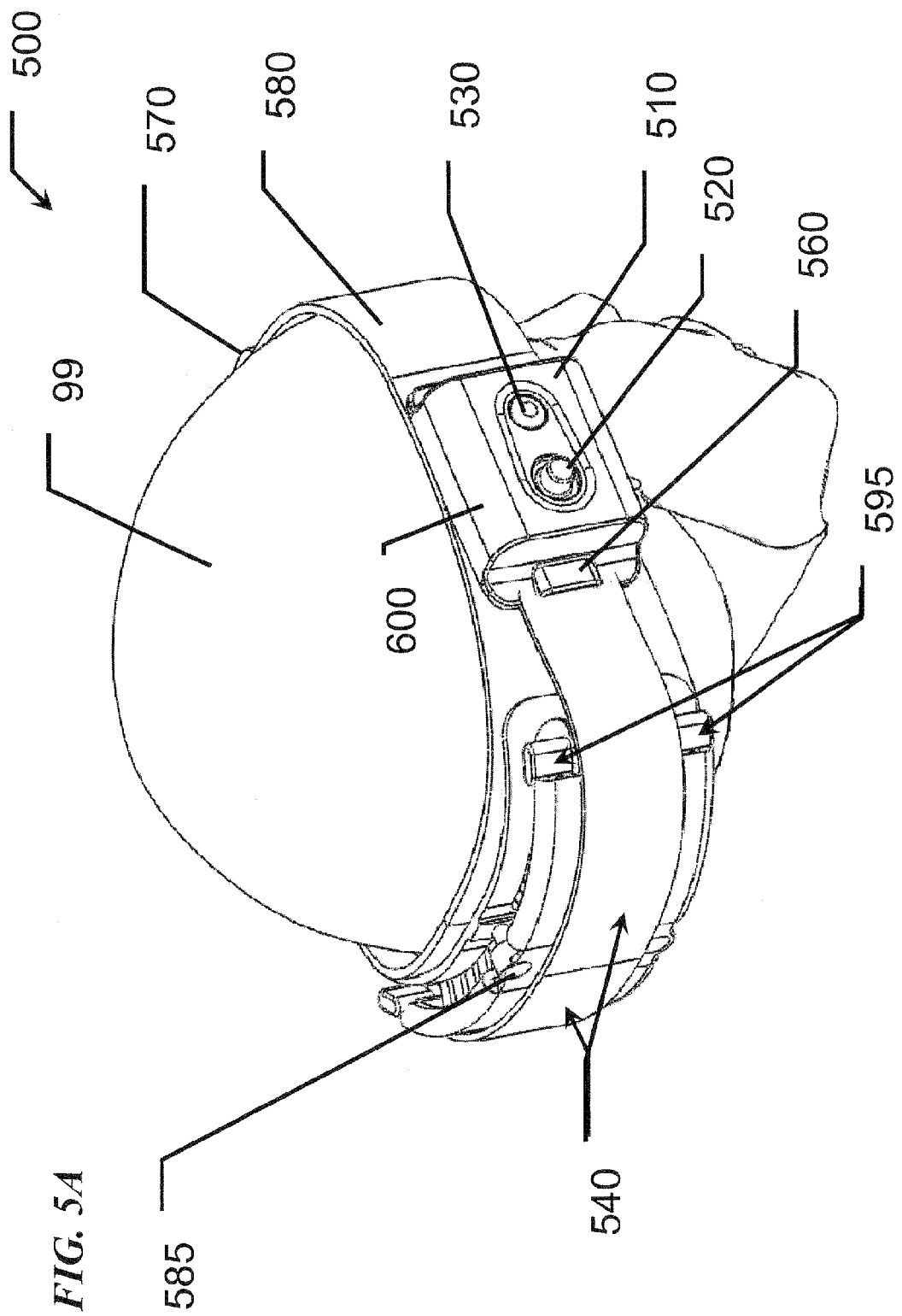
FIG. 5A is drawing of a hands-free embodiment as it is applied on the head of a patient 99.
Figure 5B:
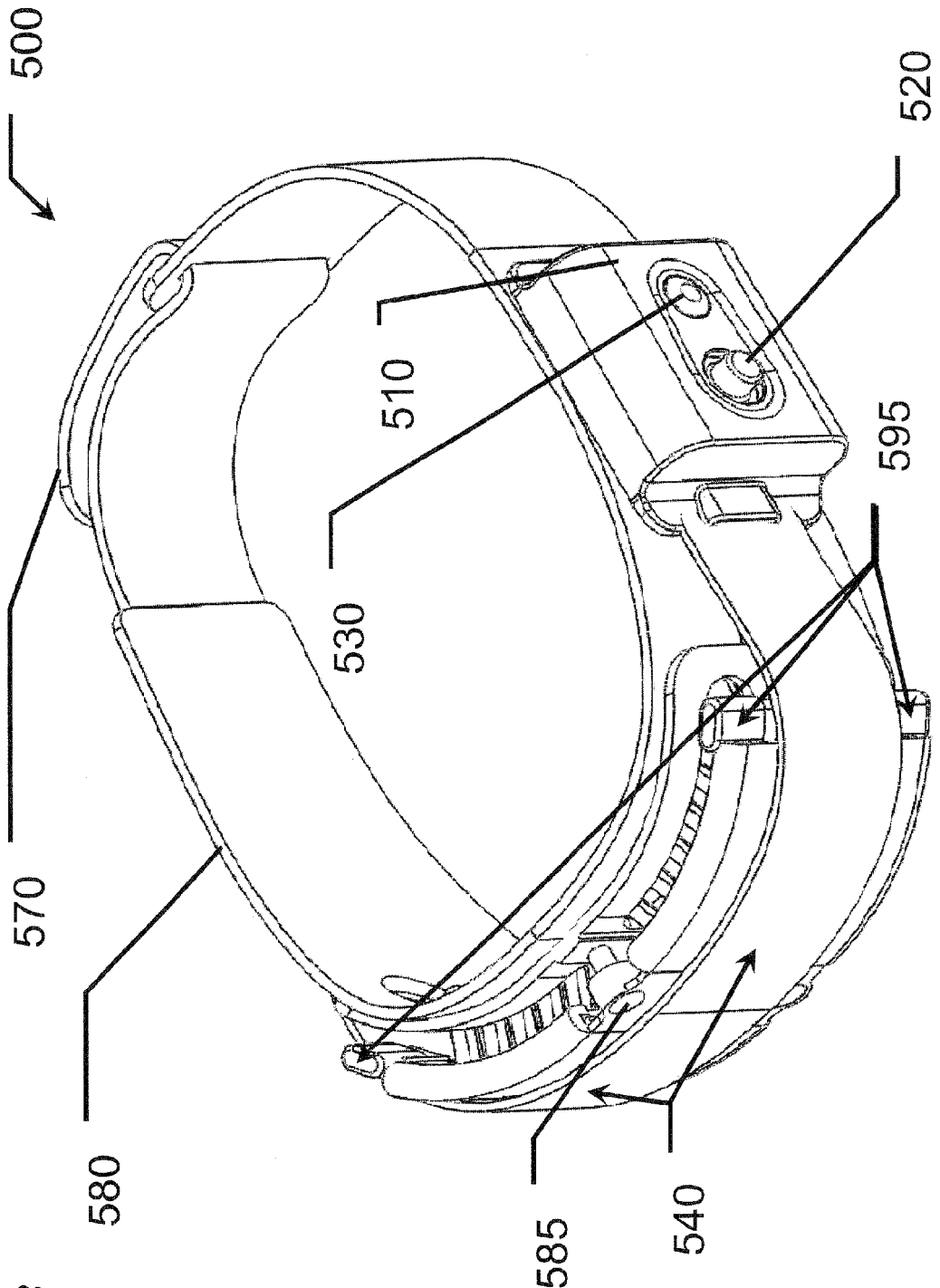
FIG. 5B is drawing of a hands-free embodiment 500.
Figure 5C:
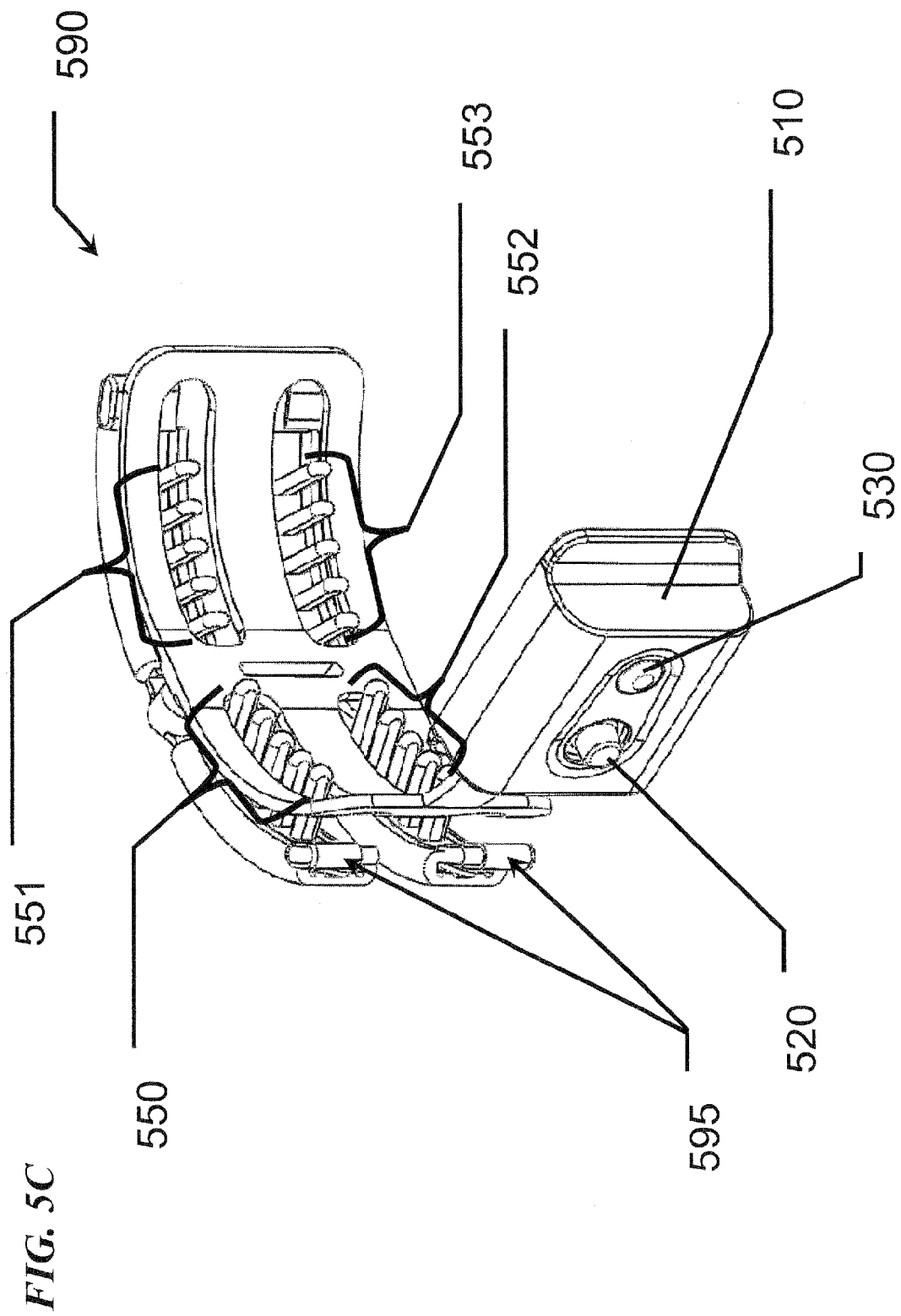
FIG. 5C is a drawing of a detachable portion (electrodes-control-box ensemble 590) of the hands-free embodiment 500.

FIG. 5A is a drawing of a hands-free TENS device 500 placed on the head of a patient 99 (see FIG. 5B for a depiction of device 500 alone). In some embodiments, the TENS device 500 includes a control case 510 with an electronic circuit 630 and a battery holder 640 (see FIG. 6), a right top electrode ensemble 550, a right bottom electrode ensemble 552, a left top electrode ensemble 551, a left bottom electrode ensemble 553 an enclosure 510, and controls including a timed therapy-start push-button 530, a therapy selector knob (not shown), an intensity selector knob 520, a master ON/OFF switch (not shown), a plastic connector 560 that holds together all of the above-mentioned electrode assemblies and the control box 510. In addition, in some embodiments, device 500 has a head-band 580 onto which the plastic connector 560 and what is attached to it can be incorporated forming a single functional unit. In some embodiments, the head-band 580 also has a strap 570 which can be used to secure the device 500 to the head of the patient 99. Also, in some embodiments tension straps 540 are used to tension the electrodes against the head of the patient.

FIG. 6, which is composed of FIG. 6A, FIG. 6B, FIG. 6C, and FIG. 6D) are perspective views of the battery-and-electronics holder 600 used for some embodiments of case 510 for the headband device 500 of FIG. 5A and FIG. 5B.

Figure 5D:
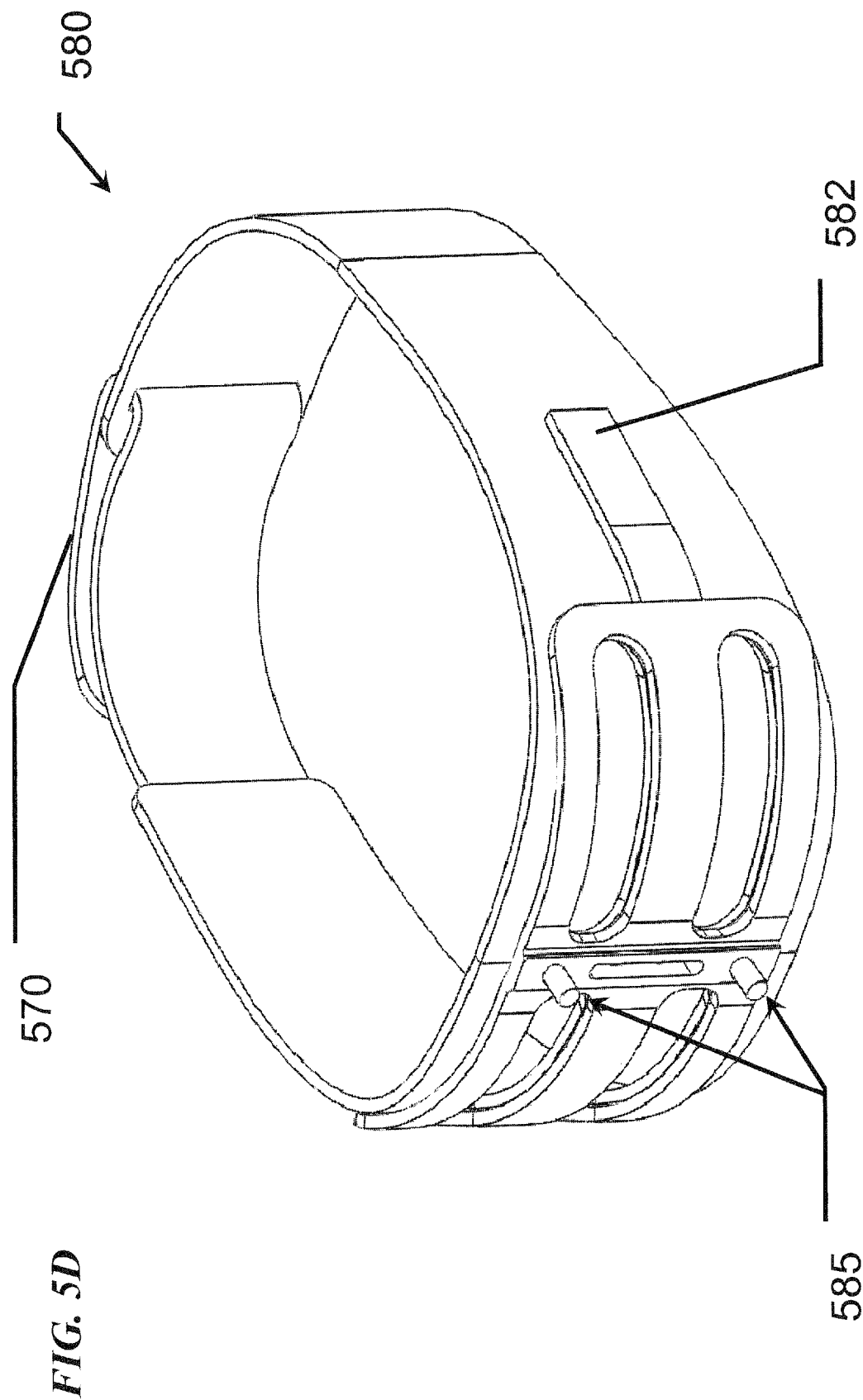
FIG. 5D is a posterior drawing of the head-band 580.

In some embodiments in order to facilitate the cleaning of the device 500, the head-band 580 and the electrodes-control-box ensemble 590 (see FIG. 5C) can be detached and reattached by using Velcro® strips 582 (or like attachment means) and/or metal or plastic pins 585 (see FIGS. 5D-5E). In some embodiments the head-band 580 can be washed in a regular washing machine used for clothing.

Figure 5F:
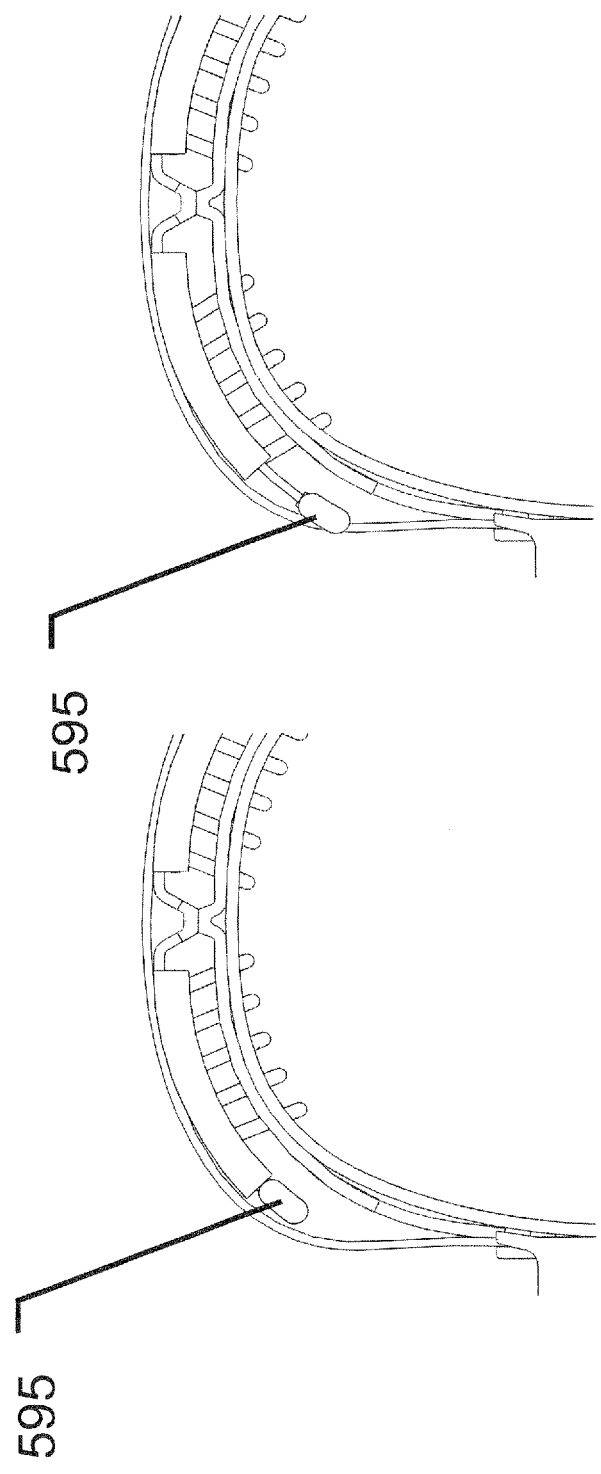
FIG. 5F is a drawing depicting the extreme positions of electrode handle 595.

In some embodiments of device 500, in order to facilitate the placement of the electrodes, the electrode ensembles 550, 551, 552, and 553 are slid from side to side by pulling/pushing electrode handle 595 (see FIG. 5F).

In some embodiments, device 500 includes a transcutaneous electrical nerve stimulator (TENS) having a plurality of electrodes, wherein the stimulator and the plurality of electrodes are incorporated into a single, self-contained device 500 that is battery operated and hands-free to operate.

Figure 9A:
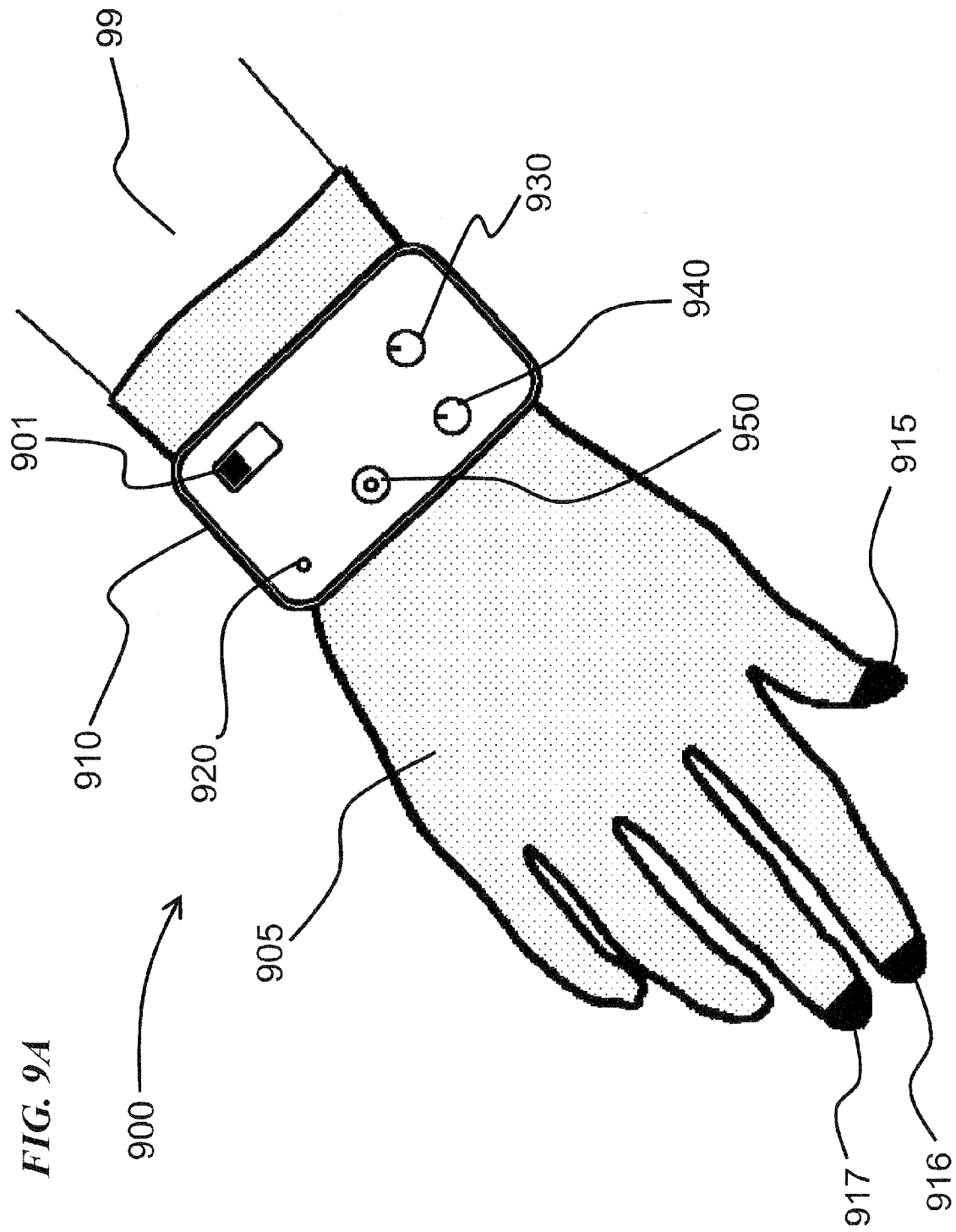
FIG. 9A is a drawing of a glove-TENS embodiment 900.

FIG. 9A is a drawing of a glove-TENS embodiment 900. In some embodiments of device 900, the control box 910 contains the same electronics as device 500. In some embodiments of device 900, an LED 920 turns ON when the device is ON. In some embodiments of device 900, the therapy is applied as follows: the stimulation frequencies are selected with the therapy-selector knob 930, and then the device is turned ON via a switch 901. In some embodiments, to start the therapy, a push button 950 is pressed. In some embodiments, the electrodes 915, 916, and 917 are placed on in contact with the scalp and then the intensity of the stimulation is adjusted using the intensity adjustment knob 940. In some embodiments of device 900, the electrodes are connected to the control box 910 via small metal strips that are embedded into the globe 905. In some embodiments of device 900, two electrodes are connected to the same polarity; for example, in one embodiment electrodes 916 and 917 are electrically connected to one another and correspond to electrode ensemble 112 of FIG. 1A or FIG. 1E, while electrodes 915 correspond to electrode ensemble 114 of FIG. 1A or FIG. 1E, and therefore, the current flows between electrodes 916 and 917, and electrode 915. Other combinations are possible (such as electrically connecting 916 and 915 for one set of electrodes (e.g., corresponding to ensemble 112) and using 917 for the other set of electrodes (e.g., corresponding to ensemble 114), or such as electrically connecting 917 and 915 for one set of electrodes (e.g., corresponding to ensemble 112) and using 916 for the other set of electrodes (e.g., corresponding to ensemble 114)), and are contemplated for other embodiments.

Figure 9B:
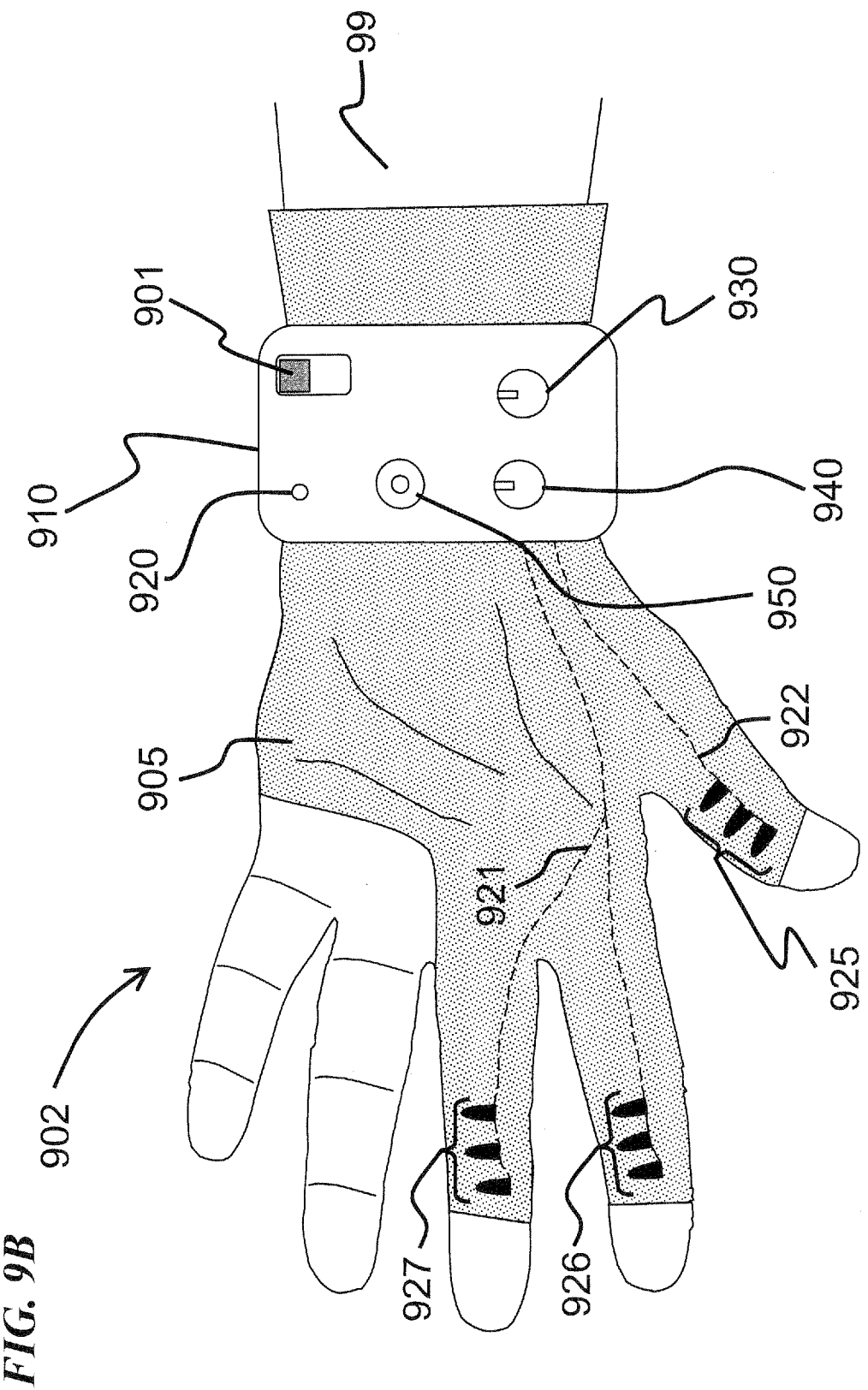
FIG. 9B is a drawing of a glove-TENS embodiment 902 having comb-like electrodes.

FIG. 9B is a drawing of another glove-TENS embodiment 902 having comb-like electrodes 907, 908, and 909 that are configured to separate the hair on the patient's head in order to make easy contact to the scalp under the hair of the patient. In some embodiments, controller 910 is attached using electrical conductors 921 and 922 (e.g., insulated wires, in some embodiments,) to two or more sets of electrodes 907, 908, and 909, and is controlled by control knob 930, control knob 940, start-therapy button 950, ON-OFF button 901 which, when ON, activates LED 920.

Figure 9C:
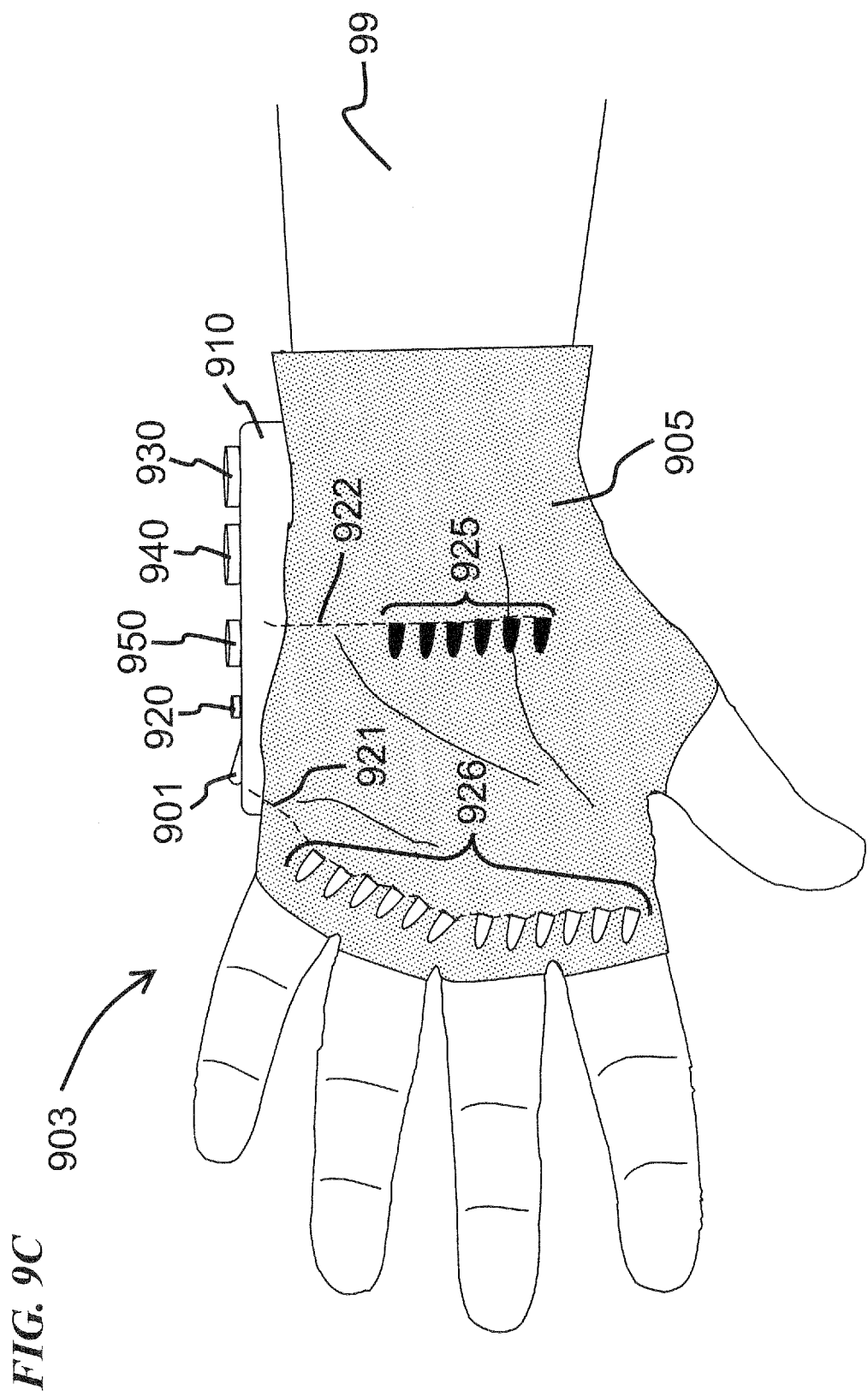
FIG. 9C is a drawing of a glove-TENS embodiment 903 having comb-like electrodes.

FIG. 9C is a drawing of a still another fingerless glove-TENS embodiment 903 having comb-like electrodes 925 and 926 located on the palm in order that the patient may place her or his hand with its palm on the nape of the neck and easily and comfortably move the device 903 to the location that feels the best or is most effective at relieving pain. In some embodiments, controller 910 is attached using electrical conductors 921 and 922 (e.g., insulated wires, in some embodiments,) to two or more sets of electrodes 926 and 925, and is controlled by control knob 930, control knob 940, start-therapy button 950, ON-OFF button 901 which when ON activates LED 920.

In some embodiments, the stimulator of the electronic circuits 300 and 700 (see FIG. 3 and FIG. 7A) and electronic circuit 701 (FIG. 7B) is divided into two main blocks: the power supply 320 and the pulse generator 330. The power supply provides the electrical potential (i.e., current-limited voltage) needed to stimulate the desired bodily tissue. The electrical potential is supplied via an inductive based DC/DC boost converter 340, and controlled via a variable reference resistance 350 which is used to set the desired output voltage. In some embodiments, the reference resistance 350 is a potentiometer which is controlled by the intensity selector knob 186/520. In some embodiments, as a safety measure, the output current is limited to at most about 60 mA by a series resistance 360 (e.g., a resistance of about 2K ohms with a voltage supply of about 120 volts). In some embodiments, as a safety measure, the output current is limited to at most about 50 mA by a series resistance 360 (e.g., a resistance of about 2.4K ohms with a voltage supply of about 120 volts). In some embodiments, as a safety measure, the output current is limited to at most about 40 mA by a series resistance 360 (e.g., a resistance of about 3K ohms with a voltage supply of about 120 volts). In some embodiments, as a safety measure, the output current is limited to at most about 30 mA by a series resistance 360 (e.g., a resistance of about 4K ohms with a voltage supply of about 120 volts). In some embodiments, as a safety measure, the output current is limited to at most about 20 mA by a series resistance 360 (e.g., a resistance of about 6K ohms with a voltage supply of about 120 volts). In some embodiments, as a safety measure, the output current is limited to at most about 10 mA by a series resistance 360 (e.g., a resistance of about 12K ohms with a voltage supply of about 120 volts). In some embodiments, as a safety measure, the output current is limited to at most about 5 mA by a series resistance 360 (e.g., a resistance of about 24K ohms with a voltage supply of about 120 volts). In some embodiments, as a safety measure, the output current is limited to at most about 2 mA by a series resistance 360 (e.g., a resistance of about 60K ohms with a voltage supply of about 120 volts). In some embodiments, as a safety measure, the output current is limited to at most about 1 mA by a series resistance 360 (e.g., a resistance of about 120K ohms with a voltage supply of about 120 volts). In some embodiments, the circuit is configured to limit the maximum open-circuit output voltage to at most about 200V (with an appropriate current-limiting resistance). In some embodiments, the circuit is configured to limit the maximum open-circuit output voltage to at most about 175V. In some embodiments, the circuit is configured to limit the maximum open-circuit output voltage to at most about 150V. In some embodiments, the circuit is configured to limit the maximum open-circuit output voltage to at most about 125V. In some embodiments, the circuit is configured to limit the maximum open-circuit output voltage to at most about 100V. In some embodiments, the circuit is configured to limit the maximum open-circuit output voltage to at most about 75V. In some embodiments, the circuit is configured to limit the maximum open-circuit output voltage to at most about 50V. In some embodiments, the circuit is configured to limit the maximum open-circuit output voltage to at most about 25V. The circuit configuration for some embodiments can be found in the applications report SLVA209 from Texas Instruments (www.ti.com), which is incorporated herein by reference. For example, in some embodiments, a Texas Instruments circuit model TPS61040 high-frequency boost converter and an external transistor (such as an N-channel Si9422 available from Vishay or other companies) in cascade mode and other components in a configuration well known to those of skill in the art (such as shown in applications report SLVA209) are used to obtain an open-circuit voltage of approximately 120 volts. In other embodiments, any other suitable DC-DC converter or other power supply is used to obtain the high voltage of circuit 320.

In some embodiments, where a monophasic pulse is desired, the pulse generator 330 includes a clock 370 and a monostable circuit 380. (In other embodiments (not shown, but in a manner similar to that shown in FIG. 7B), pulse generator circuit 330 is implemented by a suitable microprocessor, which is configured to receive user input as to the pulse repetition rate, pulse width, intensity and the like, and programmed to substitute for transistor 390 or output pulses to one or more external transistors 390 (as in FIG. 3) or 720/722/724 and 726/728/730 (as in FIG. 7B).) In some embodiments, the frequency of the clock 370, which can vary from 50 Hz to 10 kHz, is set via an array of resistors 352, (or other suitable means) wherein a particular resistor is selected by a multi-pole rotary switch attached to the therapy selector knob 184 in device 100 (not shown for device 500), and thus the position of the multi-pole rotary switch 351 is controlled by the therapy selector knob, 184 in device 100, and by a similar therapy selector knob (not shown) in device 500. The pulse width (PW) of the monostable 380 is set via another array of resistors 353, however, in some embodiments, a particular resistor is also selected by the same multi-pole rotary switch 351 attached to the therapy selector knob 184 in device 100, and by a similar therapy selector knob (not shown) in device 500, and therefore, the therapy selector knob 184 in device 100, and by a similar therapy selector knob (not shown) in device 500 controls both the PW of the monostable 380 and the frequency of the clock 370. In other embodiments the frequency and PW are selected independently via different selector knobs each one attached to a different multi-pole rotary switch. In one embodiment, a two-pole four-throw (i.e., four-position) rotary switch 351 is used such that pulse frequency and pulse width are both set for each of the four positions of rotary switch 351 as follows: 50 Hz/100 μs, 200 Hz/75 μs, 3 kHz/50 μs, and 10 kHz/40 μs. In another embodiment a four-pole rotary or slide switch is used such that frequency and pulse width are for the four positions as follows: 50 Hz/50 μs, 200 Hz/50 μs, 3 kHz/50 μs, and 10 kHz/50 μs. In other embodiments other combinations such as 50 Hz/75 μs, 200 Hz/75 μs, 3 kHz/75 μs, and 10 kHz/75 μs or 50 Hz/100 μs, 200 Hz/100 μs, 3 kHz/100 μs, and 5 kHz/100 μs can be used. In yet other embodiments, other frequencies and/or pulse widths and their combinations can be used.

As used herein, a pulse stream is a series of pulses that are sent to two sets of electrodes, each set of electrodes having one or more electrodes in contact with spaced-apart locations on the patient's skin. As used herein, a monophasic pulse stream is one in which all or substantially of the pulses have a single polarity relative to ground (zero volts between the two sets of electrodes) or a high-impedance state (wherein one or both electrode ensembles is disconnected by a transistor in the OFF state) (see FIG. 13)). In contrast, as used herein, a biphasic pulse stream is one in which pulses extend in each of two polarities relative to a zero voltage (or high-impedance state) between the two sets of electrodes. As used herein, a multiphasic pulse stream is one in which pulses extend in each of two polarities relative to a zero voltage between pairs of sets of electrodes, wherein there are three or more sets of electrodes (essentially, this is a configuration using two or more biphasic pulse streams among three or more sets of electrodes). As used herein, a spaced-pair biphasic pulse stream is one in which pulses extend in each of two polarities relative to a zero voltage between the two sets of electrodes, and wherein there is a short period (e.g., 50 to 100 microseconds) of substantially zero voltage inserted between a positive pulse and a negative pulse (in some embodiments, the orientation of "positive" and "negative" depends on an arbitrary assignment of one set of electrodes (e.g., the second set) as the reference set, and the voltage applied to the first set of electrodes is positive, zero or negative relative to the second set, wherein the designation is arbitrary since the apparatus can be reversed in orientation relative to the patient's skin and the directions of polarities reverse). In contrast, as used herein, an unspaced-pair biphasic pulse stream is one in which pulses extend in each of two polarities relative to a zero voltage between the two sets of electrodes, and wherein there is no period of substantially zero voltage between a positive pulse and a negative pulse, but rather, the positive pulse is immediately followed by the negative pulse. An alternating spaced-pair biphasic pulse stream is one in which pulses extend in each of two polarities relative to a zero voltage between the two sets of electrodes, and wherein there is a short period (e.g., 50 to 100 microseconds) of substantially zero voltage inserted between a pulse of one polarity and the following opposite-polarity pulse, and wherein which polarity pulse is first alternates (see FIG. 11).

Figure 7A:
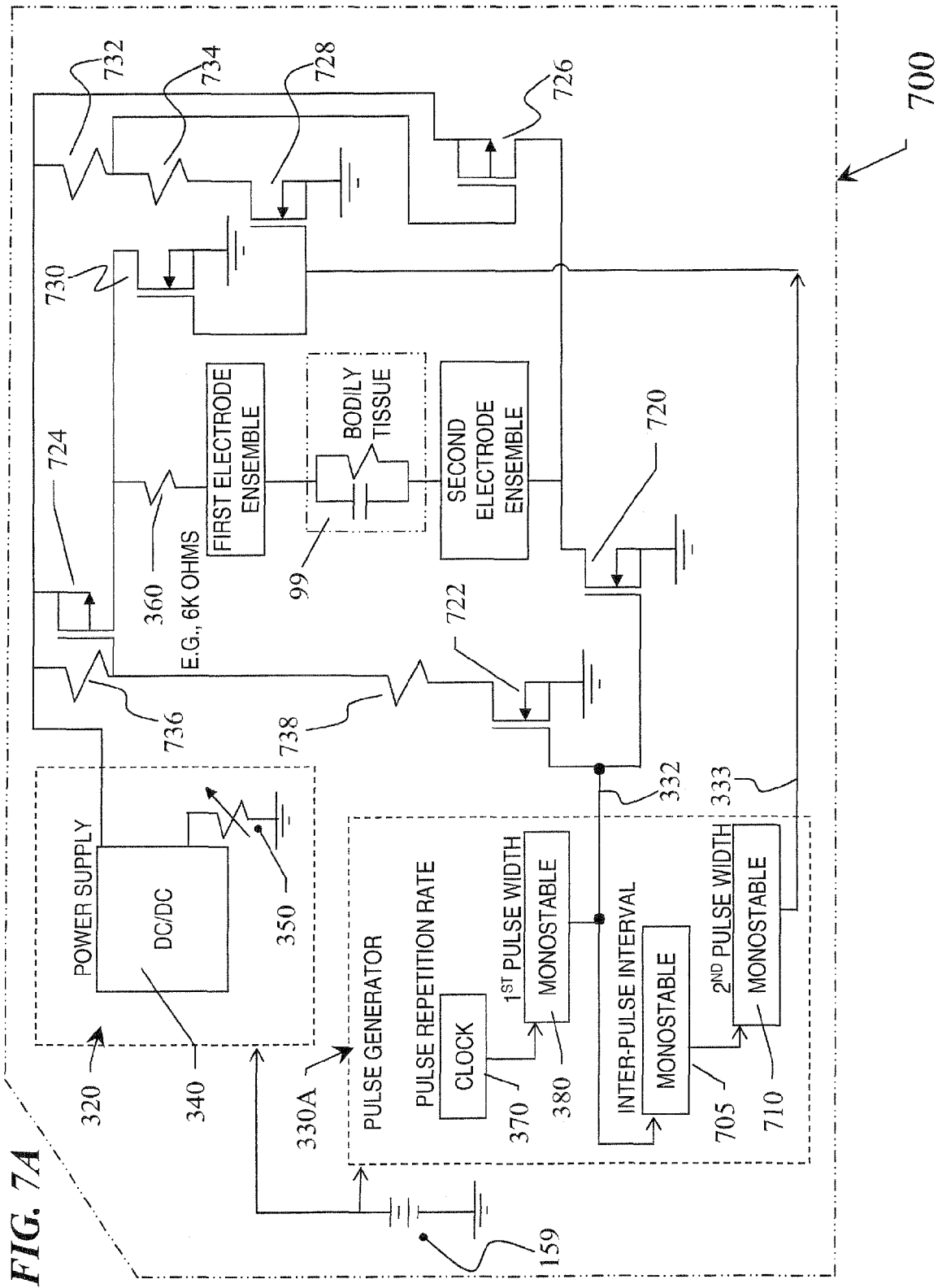
FIG. 7A is a block diagram of the biphasic electronic circuit 700 used in some embodiments.

FIG. 7A is a schematic diagram of a circuit 700 according to some embodiments of the present invention. Circuit 700 is similar to circuit 300 of FIG. 3, except that pulse generator 330A outputs a positive-pulse-control signal 332 and a negative-pulse-control signal 333.

Figure 10:
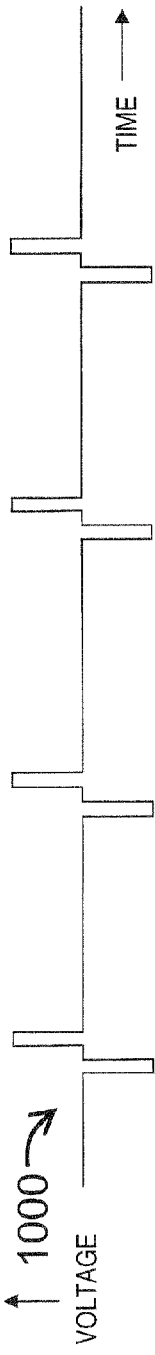
FIG. 10 is a diagram of a spaced biphasic pulse stream 1000.

FIG. 10 is a voltage-versus-time graph of a spaced biphasic pulse stream 1000. In the embodiment shown, the first pulse of each pair of pulses is a negative pulse (e.g., measured from electrode 114 to electrode 112 of FIG. 7A), and is followed after a short delay by a positive pulse. In some embodiments, the pulse width of each positive pulse is approximately equal to the pulse width of the respective negative pulse, in order to balance the electrical charge at both electrodes and the tissue in between. In some embodiments (as shown). each of the plurality of pairs of pulses has substantially the same duration for all of the positive pulses and substantially the same duration for all of the negative pulses (e.g., in some embodiments, a first pair of pulses could have a 100-microsecond first pulse, a 75-microsecond gap, and a 100-microsecond second pulse, (a total of 275 microseconds for the pair of pulses) followed by a 725-microsecond gap to provide a 1 KHz pulse repetition rate, or by a 4725-microsecond gap to provide a 200 Hz pulse repetition rate, wherein this pattern repeats indefinitely for following pairs of pulses or until the device is shut off or automatically shuts off after a predetermined time).

In other embodiments, each of a plurality of pairs of pulses have different pulse durations (e.g., in some embodiments, a first pair of pulses could have a 100-microsecond first pulse, a 75-microsecond gap, and a 100-microsecond second pulse, (a total of 275 microseconds for the pair of pulses) followed by a 725-microsecond gap to provide a 1 KHz pulse repetition rate, or by a 4725-microsecond gap to provide a 200 Hz pulse repetition rate, but a second pair of pulses could have a 200-microsecond first pulse, a 75-microsecond gap, and a 200-microsecond second pulse, (a total of 475 microseconds for the pair of pulses) followed by a 525-microsecond gap to provide a 1 KHz pulse repetition rate, or by a 4525-microsecond gap to provide a 200 Hz pulse repetition rate, wherein this pattern repeats indefinitely for following sets of pairs of pulses, or wherein other pulse durations are used in other pairs of pulses, until the device is shut off or automatically shuts off after a predetermined time).

Figure 11:
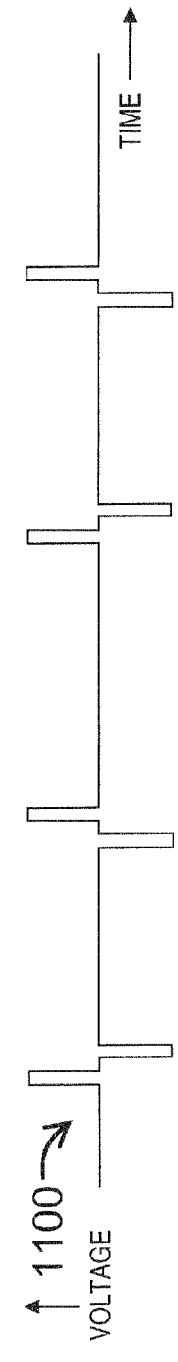
FIG. 11 is a diagram of an alternating spaced biphasic pulse stream 1100.

FIG. 11 is a voltage-versus-time graph of an alternating spaced biphasic pulse stream 1100. Note that in contrast to the pulse configuration of FIG. 10, the first pair of pulses in FIG. 11 has the positive pulse first followed by the negative pulse, the second pair of pulses in FIG. 11 has the negative pulse first followed by the positive pulse, the third pair of pulses in FIG. 11 has the positive pulse first followed by the negative pulse, and the fourth pair of pulses in FIG. 11 has the negative pulse first followed by the positive pulse. In other embodiments, other patterns of which pulse of a pair comes first are used. As with FIG. 10, each pulse can have the same duration for an entire therapy session, or different pairs of pulses can each have different pulse durations.

FIG. 12 is a voltage-versus-time graph of an alternating unspaced biphasic pulse stream 1200. This configuration of pulses is substantially the same as for FIG. 11, except that there is no gap between the two pulses of each pair of pulses. Again, each of the pulses can have equal durations (e.g., in some embodiments, a first pair of pulses could have a 100-microsecond first pulse, no gap, and a 100-microsecond second pulse, (a total of 200 microseconds for the pair of pulses) followed by a 800-microsecond gap to provide a 1 KHz pulse repetition rate, or by a 4800-microsecond gap to provide a 200 Hz pulse repetition rate, wherein this pattern repeats indefinitely for following pairs of pulses or until the device is shut off or automatically shuts off after a predetermined time). In other embodiments, the pulses can have different durations during one therapy session.

Figure 7B:
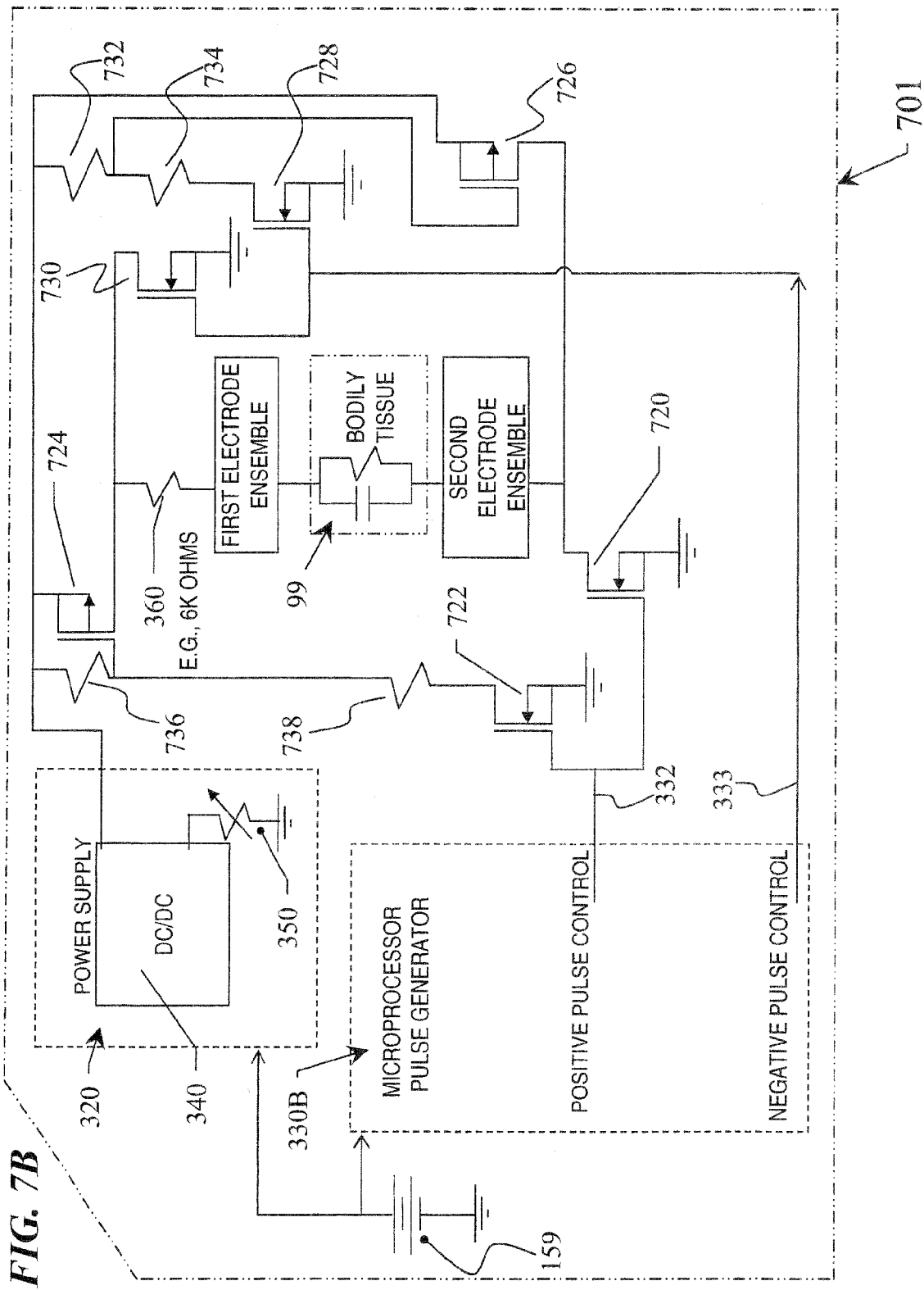
FIG. 7B is a block diagram of the biphasic electronic circuit 701 used in some embodiments.

Some embodiments providing the pulse stream of FIG. 10 use the circuit of FIG. 7A. Some embodiments providing the pulse stream of FIG. 10, FIG. 11, FIG. 12, FIG. 13 or FIG. 14 use the circuit of FIG. 7B. In some embodiments, the microprocessor circuit of FIG. 7B provides any or all of the pulse sequences of FIG. 10, FIG. 11, FIG. 12, FIG. 13 or FIG. 14 at different times.

Figure 13:
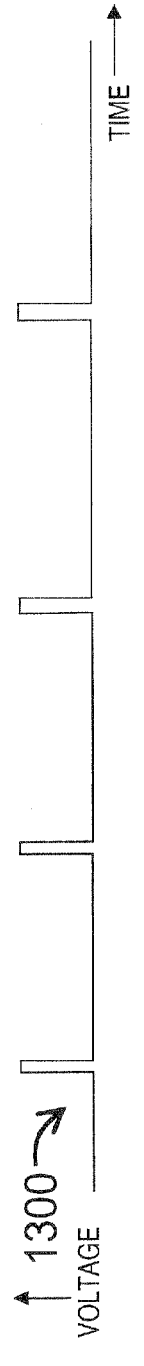
FIG. 13 is a diagram of a monophasic pulse stream 1300.

FIG. 13 is a voltage-versus-time graph of a monophasic pulse stream 1300. In the embodiment shown, a single polarity of pulses is used (such as provided by circuit 300 of FIG. 3).

Figure 14:
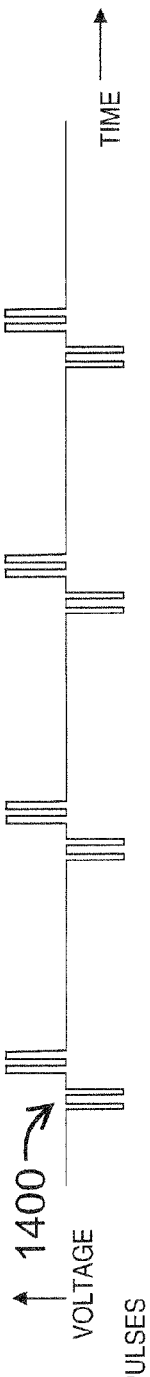
FIG. 14 is a voltage-versus-time graph of a spaced biphasic pulse stream 1400 with plural sub-pulses.

FIG. 14 is a voltage-versus-time graph of a spaced biphasic pulse stream 1400 with plural sub-pulses. As shown, in some embodiments, one or more of the positive pulses and/or one or more of the negative pulses is composed of a plurality of sub-pulses (e.g., two negative pulses separated by a gap in time from one another followed by two positive pulses separated by a gap in time from one another; or (not shown) one negative pulse separated by a gap in time followed by two positive pulses separated by a gap in time from one another followed by another gap in time and another negative pulse). In some such embodiments, the first pulse of such a set is of a smaller amplitude and the first polarity, and the second pulse is of a higher amplitude (e.g., twice the amplitude of the first pulse) and also of the first polarity. In some such embodiments, the third pulse of such a set is of a smaller amplitude and the second opposite polarity, and the fourth pulse is of a higher amplitude (e.g., twice the amplitude of the third pulse) and also of the second polarity. In other such embodiments, the third pulse of such a set is of a much smaller amplitude and the second opposite polarity, and of a much longer duration, such that by its lower amplitude and longer duration, the third pulse balances the charge of the first and second pulses but its lower amplitude does not trigger an opposite-polarity artifact in the patient's tissue.

In some embodiments, where a monophasic pulse stream is desired, the clock 370 triggers the monostable circuit 380, the output of the monostable circuit 380 drives pulse-control signal 331 to the gate of a field effect transistor (FET) 390, which is used to connect the bottom electrode ensemble(s) 114, 552, 553 to ground, therefore allowing current to pass between the top electrode ensemble(s) 112 550, 551, and the bottom electrode ensemble(s) 114, 552, 553. Hence, the pulse width (PW) of the stimulation signal follows the pulse width (PW) of the monostable circuit 380.

Figure 3:
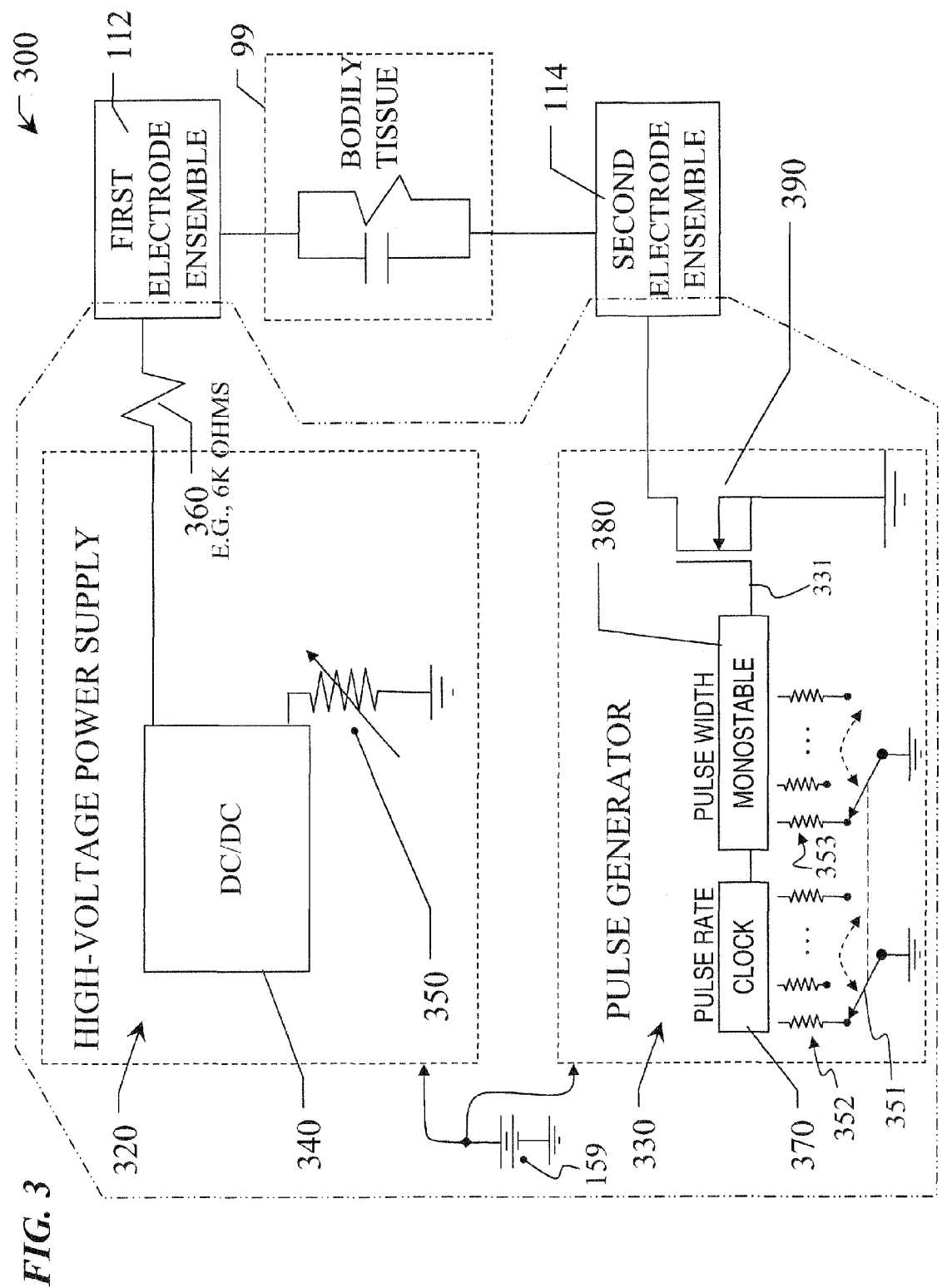
FIG. 3 is a block diagram of the monophasic electronic circuit 300 used in some embodiments.

In yet other embodiments where a biphasic pulse is desired, referring to FIG. 7A, the output of the monostable circuit 380 triggers a second monostable circuit 705 which in turn triggers a third monostable circuit 710. The output of the monostable circuit 380 also drives the gates of two field effect transistors (FET) 722 and 720. The output of the monostable circuit 710 drives the gate of another two field effect transistors (FET) 728 and 730. The FET 722 turns on FET 724 via an array of resistors 738 and 736. When FET 724 and FET 720 are turned on, the first electrode ensemble(s) 112 (or 550, 551 in FIG. 5C) are connected to the positive voltage and the second electrode ensemble(s) 114 (or 552, 553 in FIG. 5C) are connected to ground (positive phase). The FET 728 turns on FET 726 via and an array of resistors 734 and 732. When FET 726 and FET 730 are turned on, the bottom electrode ensemble(s) 114, 552, 553 are connected to the positive voltage and the top electrode ensemble(s) 112, 550, 551 are connected to ground (negative phase). The monostable circuit 705 generates an inter-pulse interval between the positive and the negative phase. In some biphasic embodiments, the elapsed time of the monostable circuits 380, 705 and 710 as well as the rate of the clock 370 can be modified through an array of resistors and rotary switches such as it is depicted in FIG. 3 by resistors 353, 352 and switch 351, or can be controlled by a programmed microprocessor 330B as shown in FIG. 7B.

In some embodiments, the inter-pulse interval is not needed and therefore the monostable circuit 705 is not needed, in this case, the output of the monostable circuit 380 directly triggers the monostable circuit 710.

Figure 8:
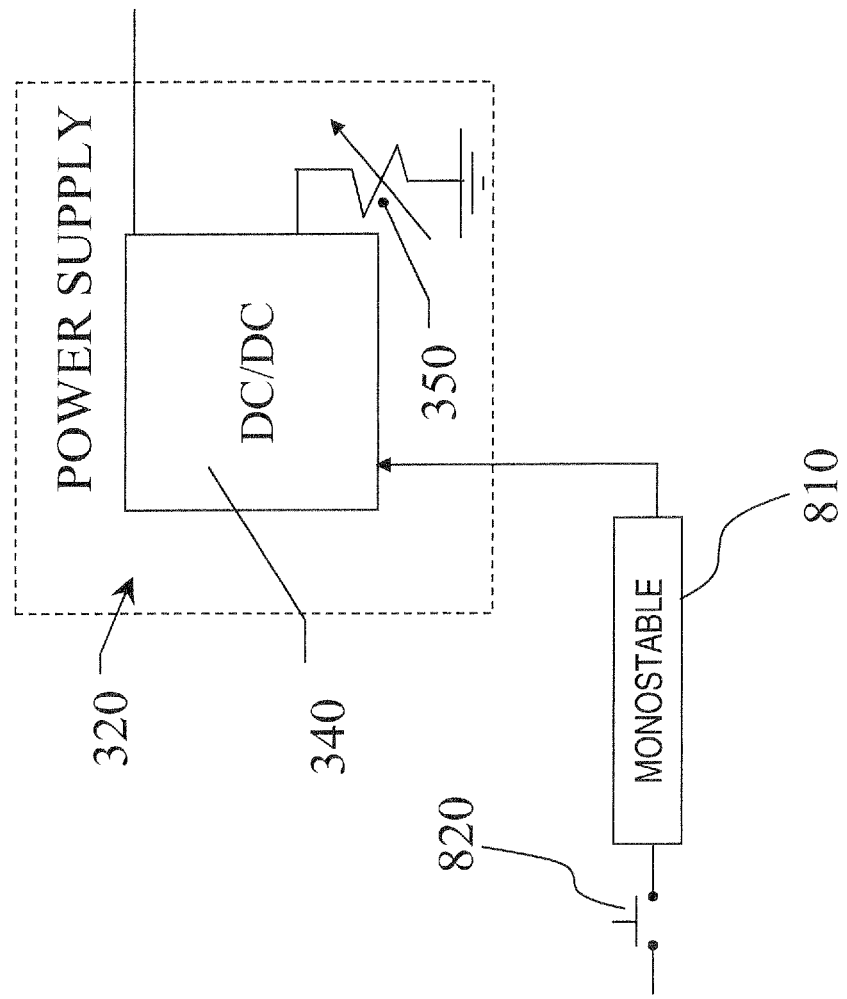
FIG. 8 is a partial block diagram of some embodiments of circuits 300 and 700 where a monostable circuit 810 is used as a therapy timer 810.

In some embodiments, a monostable circuit 810 acts as a timer such that when the output of this monostable circuit 810 is ON the therapy is also ON, and it is turned OFF when the monostable pulse if over (see FIG. 8). In this case, in some embodiments a push-button 820 can be used to trigger the monostable circuit 810.

In some embodiments, a microprocessor can be used to substitute all monostable circuits 380, 705, 710, and 810 as well as the clock 370.

Since the device delivers the stimulation transcutaneously and since the muscles are closer to the skin than nerves, the output of the TENS device is such that it minimizes muscle activation and maximizes nerve activation by taking advantage of the differences in the excitability properties (i.e., chronaxie τ and rehobase $I_{Rh}$) between muscle and nerve tissue. The excitation threshold ($I_{th}$) as a function of the pulse width (PW) for excitable tissue follows a hyperbolic function known as the strength-duration curve:

$$I_{th} = I_{Rh}\left(1 + \frac{\tau}{PW}\right).$$

In general both the τ and the $I_{Rh}$ for muscle are bigger than those for nerve tissue and therefore a way to increase the difference between the $I_{th}$ of muscle tissue and the $I_{th}$ of nerve tissue is using short PW. The TENS device disclosed here uses short pulse widths (PWs; i.e., PW<400 microseconds).

Since in some stimulation regions in the head it is likely that hair will be present, the portion of the electrode ensemble(s) 112, 552, 553, 114, 550, and 551 that makes contact with the body of the patient is shaped in the form of several separated structures 112 and 114 (comb-like ensemble) to facilitating the displacement of hair thus maximizing skin-electrode contact.

In some embodiments, in the case of device 100, the invention is carried out by putting conductive gel in the region of the head to be treated (see FIG. 2), then, turning the TENS device ON (moving ON/OFF switch 182) and adjusting the therapy selector knob 184 and the intensity selector knob 186 (actual adjustments are patient dependent). Once the intensity and the therapy have been selected, then the electrode ensembles 112 and 114 of the TENS device are positioned in the area to be treated. The treatment includes randomly moving the electrodes by moving the TENS device around the desired area on both sides of the head for an effective amount of time. The therapy can be administered to one side at a time or by constantly alternating sides. The specific neural structures to be treated are stated above in this section. In some case, the intensity is readjusted while the therapy is being administered.

In order to facilitate the contact between the electrode ensembles 112 and 114 and the skin, the electrode ensembles 112 and 114 are mounted on the electrode-ensemble head 110, which can rotate on the shafts 122 and 124 (which connect to pivot assembly 120 of extension piece 116) to which head 110 is attached.

In some embodiments, in the case of device 500, the invention is carried out by putting conductive gel in the region of the head to be treated (see FIG. 2), then, securing the device on the patients head, turning the TENS device ON (moving/pressing ON/OFF switch 530) and adjusting the therapy selector knob (not shown) and the intensity selector knob 520 (actual adjustments are patient dependent). Once the intensity and the therapy have been selected, then the patient can perform his/her regular tasks while the treatment is ON. The therapy is administered to both sides simultaneously. The specific neural structures to be treated are stated above in this section. In some embodiments, by pressing the push button 820 is pressed by switch 530. By pressing push button 820 the monostable 830 outputs a pulse of pre-determined duration. In turn, the monostable pulse turns on the therapy by enabling the DC/DC converter 340. Therefore, the monostable serves as a timer for the therapy, when the monostable pulse is ON the therapy is ON and when the monostable pulse is OFF then the therapy is OFF. In some embodiments, aside from the switch 530 there is a general ON/OFF switch (not shown).

In some embodiments, the electrode ensembles 112, 552, 553, 114, 550, and 551 and the shafts 122 and 124 are made of stainless steel; however, they can be made out of any other suitable material.

In some embodiments of the device 100, the top electrode ensemble 112, and the bottom electrode ensemble 114 are, electrically connected through shaft 122 and shaft 124, respectively, via conductors (wire, cable, strip, etc.) buried in the electrode-ensemble head 110. The shafts 122 and 124 are connected to the circuit board 160 through electrically conductive cables (not shown) that run inside pivot assembly 120 and extension piece 116 and under the battery holder 170 to reach the circuit board 160.

In some embodiments of the device 100, pivot assembly 120 also includes a pressure-sensitive switch that disconnects the power to electrodes 112 and 114 unless both electrodes are firmly pressed against the patient's skin, which can help prevent undesirable electrical conditions (e.g., perhaps sparking, or current or voltage surges due to changes in the resistivity between device 100 and patient 99).

In some embodiments of the device 100, a conductivity-gel applicator unit is attached to head 110, and which includes a button that, when pressed by the user, dispenses a small amount of gel through a hollow shaft that extends to the tip of each of one or more tines of electrode ensembles (combs) 112 and/or 114. This allows the user to directly apply a small but effective amount of conductive gel directly to the skin being contacted by electrode ensembles 112 and 114.

In some embodiments, electrode ensembles 112, 552, 553, 114, 550, and 551 are each of other geometrical shapes such as, but not limited to, a standard hair-comb shape or a cylinder.

In other embodiments of the device 100, the electrode ensembles 112 and 114 are electrically connected to the shafts 122 and 124, respectively, via metal strips buried in the electrode-ensemble head 110.

In other embodiments of the device 100, the shafts 122 and 124, are electrically connected to the circuit board 160, via metal strips that run inside the extension piece 116 and under the battery holder 170 to reach the circuit board 160.

In some embodiments of device 500, the electrode ensembles 550, 551, 552, and 553 are connected to the circuit board 630 inside case 510 via conductors (wire, cable, strip, etc.) embedded into the a plastic connector 560.

In some embodiments of device 500, the electrode ensembles 550, 551, 552, and 553 can be individually moved in order to provide the best stimulation outcome in a case by case base. In such embodiments the electrical connection with electrode ensembles 550, 551, 552, and 553 is such that it allows for the individual movement of any electrode ensemble 550, 551, 552, and 553; for example using flat ribbon cable or a printed flex-circuit.

Figure 4:
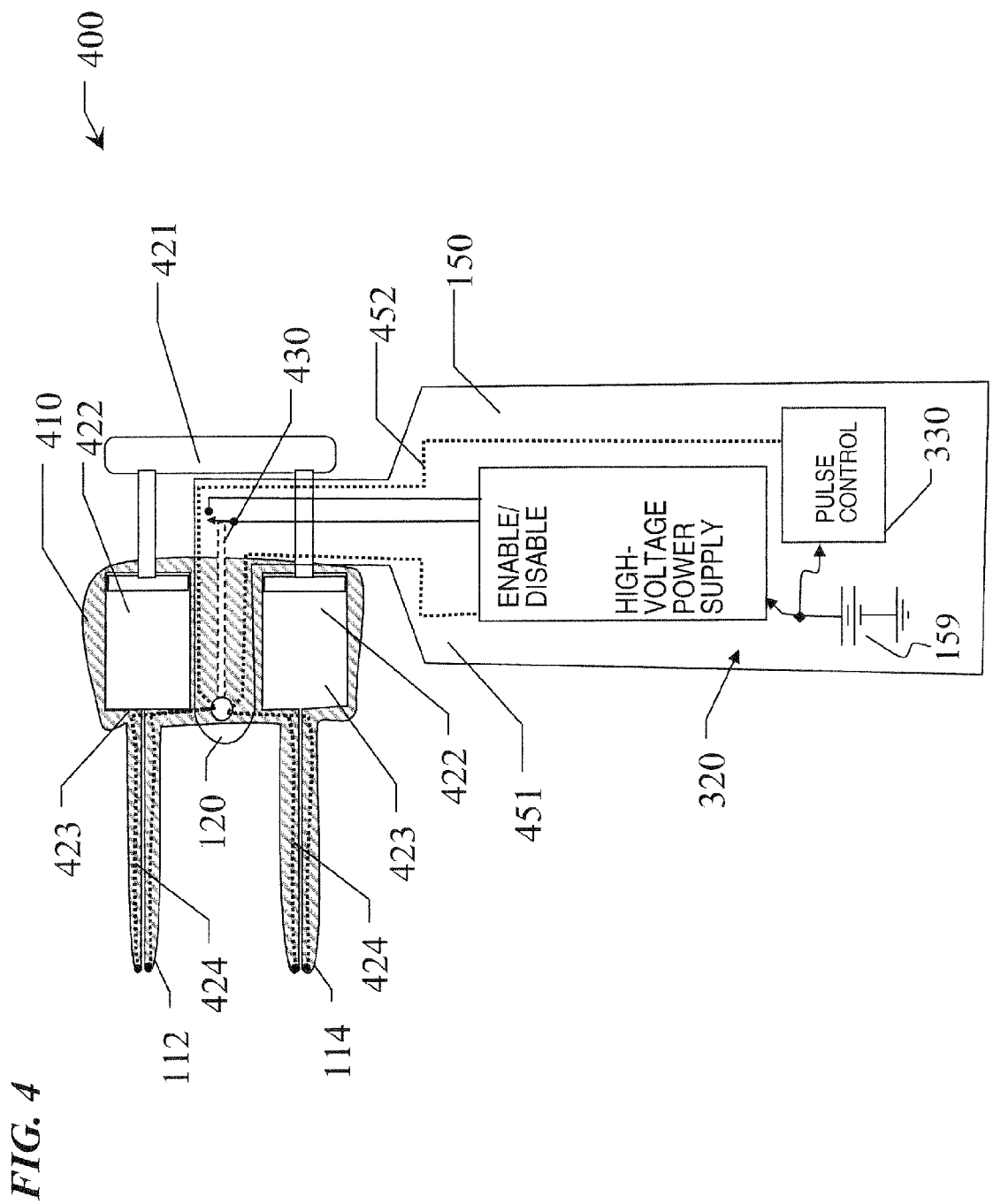
FIG. 4 is a block diagram of a TENS device 400.

FIG. 4 is a block diagram of a TENS device 400 that, in some embodiments, optionally includes a power-supply disable (or enable) switch 430 (e.g., a spring loaded switch that enables the voltage supply when pressure is applied to pivot device 120 (i.e., when the electrodes 112 and 114 of device 400 are pressed against the skin of the user). This saves battery power and eliminates any voltage to the electrodes when they are not firmly pressed against the user's skin. In some embodiments, device 400 also includes one or more conductive-gel reservoirs 423 (e.g., in some embodiments, the user presses button 421 on swiveling head 410, which applies pressure to pistons 422 in cylinders 423 (e.g., similar to a syringe), and in turn dispenses gel through capillaries 424 that extend to the conductive ends of one or more insulative (e.g., plastic) tines of the electrodes 112 and 114. In some embodiments, conductors 451 extend from power supply 320 to the ends of electrodes 114, and conductors 452 extend from electronic pulse controller 330 to the ends of electrodes 112. The conductive gel provides a better electrical connection between electrodes 112 and 114 and the skin of patient 99, and between electrodes 550 and 552 and the skin of patient 99, and between electrodes 551 and 553 and the skin of patient 99.

In some embodiments the conductive gel might be stored in a reservoir located elsewhere on the TENS device 400 as a separate compartment or inside an existing one, for example inside the electrode ensembles 112 and 114 or in the electrode-ensemble head 410 as shown. The conductive gel might be administered via delivery channels running through the electrode themselves by pressing a small lever.

In some embodiments the TENS device might be positioned on the head by attaching the electrodes and stimulator to the area to be treated. In some embodiments, the stimulation is carried out without the use of conductive gel.

In some embodiments, the present invention provides a method for treating a headache of a patient, the method including providing a portable, transcutaneous electrical nerve stimulator (TENS) having a plurality of electrodes; receiving, by the TENS, an activation indication from the patient; and based on the activation indication, providing a plurality of electrical pulses from the TENS transcutaneously to the nerves of the patient in order to treat headache pain.

In some embodiments, the providing of the TENS includes housing the TENS and the plurality of electrodes in a unitary device, wherein the device has no exposed wiring, and wherein the device facilitates a self-administered treatment by the patient.

In some embodiments, the providing of the plurality of electrical pulses treats headache pain in an abortive manner. In other embodiments, the providing of the plurality of electrical pulses treats headache pain in a preventive manner.

In some embodiments, the providing of the TENS includes providing a handheld device. In other embodiments, the providing of the TENS includes providing a hands-free device.

In some embodiments, each one of the plurality of electrodes is at a distance from one another and configured such that at least two electrodes touch the patient's skin simultaneously.

In some embodiments, the providing of the TENS includes providing a TENS that delivers pulses at one or more frequencies between about 40 Hz and about 10 kHz. In some embodiments, the providing of the plurality of electrical pulses includes providing pulses that are delivered at no more than 60 mA. In some embodiments, the providing of the plurality of electrical pulses includes providing pulses that are delivered at no more than 200 volts. In some embodiments, the providing of the plurality of electrical pulses includes providing electrical pulses having a pulse width that is equal or less than 400 micro seconds.

In some embodiments, the providing of the plurality of electrical pulses includes stimulating at least one of the following nerve structures: the right and/or left greater occipital nerve(s), the right and/or left least (third) occipital nerve(s), the right and/or left lesser occipital nerve(s), the right and/or left great auricular nerve(s).

In some embodiments, the method further includes applying a conductive gel from a reservoir within the device. In some embodiments, the method further includes releasing the conductive gel through one or more delivery channels built into at least one electrode.

In some embodiments, each one of the plurality of electrodes are shaped and configured such that the plurality of electrodes facilitate contact between the plurality of electrodes and skin of the patient in bodily locations where hair impedes such contact. In some embodiments, each one of the plurality of electrodes has a comb-tooth shape to ensure that hair is combed out of the way as the patient moves the plurality of electrodes over the skin.

In some embodiments, the method further includes supplying power to the TENS via a battery, wherein the battery is electrically connected to the TENS, and wherein the battery is housed within the unitary device. In other embodiments, the method further includes supplying power to the TENS via an external power supply that is electrically connected to the TENS.

In some embodiments, the device is small enough that a person can carry it around comfortably. In some embodiments, the electrodes are not disposable and/or are reusable.

In some embodiments, the plurality of electrodes is mounted in a device head that is configured to rotate to facilitate contact between the plurality of electrodes and skin of the patient.

In some embodiments, each one of the plurality of electrodes is hollow, the method further comprising dispensing a conductive gel through each one of the plurality of hollow electrodes. In some embodiments, the method further includes disabling power to the plurality of electrodes if no pressure is applied to the head of the device, and enabling pulsed power to the plurality of electrodes if pressure is applied. In some embodiments, wherein the each one of the plurality of electrodes is hollow, the method further includes dispensing a conductive gel through each one of the plurality of hollow electrodes; and disabling power to each one of the plurality of hollow electrodes if no pressure is applied to the head of the device.

In some embodiments, the method further includes electrically disconnecting the plurality of electrodes unless the device is pressed against a surface.

In some embodiments, the present invention provides a method for treating a headache of a patient, the method including providing a portable, transcutaneous electrical nerve stimulator (TENS) having: a first plurality of non-invasive comb-like electrodes physically connected to a common electrode base and each electrically connected to a first signal output of the TENS, and a second plurality of non-invasive comb-like electrodes physically connected to the common electrode base, wherein the TENS is configured such that the first plurality of electrodes and the second plurality of electrodes can be simultaneously placed in contact with the patient's head, and wherein the second plurality of electrodes each electrically connected to a second signal output of the TENS; receiving, by the TENS, an activation indication; and based on the activation indication, providing a plurality of electrical pulses between the first signal output of the TENS and the second signal output of the TENS such that the electrical pulses are applied from both the first plurality of electrodes and the second plurality of electrodes transcutaneously to the patient's head to stimulate nerves of the patient in order to treat headache pain. In some embodiments, the providing of the TENS includes housing the TENS and the first and second plurality of electrodes in a unitary device, and wherein the device facilitates a self-administered treatment by the patient. In some embodiments, the providing of the plurality of electrical pulses treats headache pain in an abortive manner. In some embodiments, the providing of the plurality of electrical pulses treats headache pain in a preventive manner. In some embodiments, the providing of the plurality of electrical pulses includes providing biphasic substantially square pulses including a first plurality of pulses having a first polarity and a duration of no more than 400 microseconds and a second plurality of pulses having a second polarity, opposite the first polarity, and a duration of no more than 400 microseconds. In some embodiments, providing of the TENS includes providing a hands free device, and supporting the hands-free device on the patient's head. In some embodiments, the electrodes of the first plurality of electrodes are grouped into a first group, wherein the electrodes of the second plurality of electrodes are grouped into a second group, wherein the first group is located at a distance from the second group that is greater than a distance between any two adjacent electrodes in each group. In some embodiments, the providing of the TENS includes providing a TENS that delivers pulses at one or more pulse-repetition-rate frequencies of between about 40 Hz and about 10 kHz. In some embodiments, the providing of the plurality of electrical pulses includes providing pulses that are delivered at a non-zero current of no more than 60 mA. In some embodiments, the providing of the plurality of electrical pulses includes providing pulses that are delivered at a non-zero voltage of no more than 200 volts. In some embodiments, the providing of the plurality of electrical pulses includes providing electrical pulses having a non-zero pulse width that is equal or less than 400 microseconds. In some embodiments, the providing of the plurality of electrical pulses includes stimulating one or more of the nerve structures selected from the group consisting of the right greater occipital nerve, the left greater occipital nerve, the right least (third) occipital nerve, the left least (third) occipital nerve, the right lesser occipital nerve, the left lesser occipital nerve, the right great auricular nerve, and the left great auricular nerve.

Some embodiments further include applying a conductive gel from a reservoir within the device. Some embodiments further include releasing the conductive gel through one or more delivery channels built into at least one electrode of the plurality of electrodes. In some embodiments, each one of the plurality of electrodes is hollow, the method further comprising dispensing a conductive gel through each one of the first and second plurality of hollow electrodes.

In some embodiments, the first and second plurality of electrodes are shaped and configured to facilitate contact between the first and second plurality of electrodes and skin of the patient in bodily locations where hair would otherwise impede such contact. In some embodiments, each one of the first and second plurality of electrodes has a comb-tooth shape to ensure that hair is combed out of the way as the patient moves the plurality of electrodes over the skin. Some embodiments further include supplying power to the TENS via a battery, wherein the battery is electrically connected to the TENS, and wherein the battery is housed within the unitary device. Other embodiments further include supplying power to the TENS via an external power supply that is electrically connected to the TENS.

In some embodiments, the device is small enough that a person can readily carry it around. In some embodiments, the plurality of electrodes is reusable. In some embodiments, the first and second pluralities of electrodes are mounted in a device head that is configured to rotate around a point or axis to facilitate contact between the first and second plurality of electrodes and skin of the patient.

Some embodiments further include disabling power to the first and second plurality of electrodes if no pressure is applied to the head of the device, and enabling pulsed power to the first and second plurality of electrodes if pressure is applied. In some embodiments, each one of the first and second plurality of electrodes is hollow, and the method further includes dispensing a conductive gel through each one of the first and second plurality of hollow electrodes; and disabling power to each one of the first and second plurality of hollow electrodes if no pressure is applied to the head of the device.

Some embodiments include electrically disconnecting the first and second plurality of electrodes unless the device is pressed against a surface. In some embodiments, the providing of the plurality of electrical pulses includes providing substantially square, alternating-spaced-biphasic pulses including a first plurality of pulses having a first polarity and a duration of no more than 200 microseconds and a second plurality of pulses having a second polarity, opposite the first polarity, and a duration of no more than 200 microseconds.

In some embodiments, the present invention provides an apparatus for treating a headache of a patient that includes a portable, transcutaneous electrical nerve stimulator (TENS) having a common electrode base; a first plurality of non-invasive comb-like electrodes physically connected to the common electrode base and each electrically connected to a first signal output of the TENS, and a second plurality of non-invasive comb-like electrodes physically connected to the common electrode base, wherein the TENS is configured such that the first plurality of electrodes and the second plurality of electrodes can be simultaneously placed in contact with the patient's head, and wherein the second plurality of electrodes are each electrically connected to a second signal output of the TENS, wherein the TENS presents a plurality of electrical pulses between the first signal output of the TENS and the second signal output of the TENS such that the electrical pulses are applied from both the first plurality of electrodes and the second plurality of electrodes transcutaneously to the patient's head to stimulate nerves of the patient, in order to treat headache pain. In some embodiments, the TENS unit and the first and second plurality of electrodes are housed in a unitary device, wherein the device has no exposed wiring, and wherein the device facilitates a self-administered treatment by the patient. In some embodiments, the TENS is configured to treat headache pain in an abortive manner. In some embodiments, the TENS is configured to treat headache pain in a preventive manner. In some embodiments, the TENS is configured to output a plurality of electrical biphasic substantially square pulses including a first plurality of pulses having a first polarity and a duration of no more than 400 microseconds and a second plurality of pulses having a second polarity, opposite the first polarity, and a duration of no more than 400 microseconds. In some embodiments, the TENS is a hands-free device. In some embodiments, the electrodes of the first plurality of electrodes are grouped into a first group, wherein the electrodes of the second plurality of electrodes are grouped into a second group, wherein the first group and the second group are located at a distance from one another that is greater than a distance between any two adjacent electrodes in each group. In some embodiments, the TENS delivers pulses at one or more frequencies between about 40 Hz and about 10 kHz. In some embodiments, the plurality of electrical pulses is delivered at no more than 60 mA. In some embodiments, the plurality of electrical pulses is delivered at no more than 200 volts. In some embodiments, the pulse width of each one of the plurality of electrical pulses is equal or less than 400 microseconds. In some embodiments, the plurality of electrical pulses stimulate one or more of the nerve structures selected from the group consisting of the right greater occipital nerve, the left greater occipital nerve, the right least (third) occipital nerve, the left least (third) occipital nerve, the right lesser occipital nerve, the left lesser occipital nerve, the right great auricular nerve, and the left great auricular nerve. Some embodiments further include a conductive gel applicator that selectively dispenses gel from a reservoir within the handheld device. Some embodiments further include one or more delivery channels built into at least one of the second plurality of electrodes and operatively connected to the reservoir. In some embodiments, the first and second plurality of electrodes are shaped and configured to facilitate contact between the first and second plurality of electrodes and skin of the patient in bodily locations where hair would otherwise impede such contact. In some embodiments, each one of the first and second plurality of electrodes has a comb-tooth shape to ensure that hair is combed out of the way as the patient moves the plurality of electrodes over the skin. Some embodiments further include a battery electrically connected to the TENS and housed within the unitary device. Other embodiments include an external power supply electrically connected to the TENS. In some embodiments, the device is small enough that a person can carry it around comfortably. In some embodiments, the first and second plurality of electrodes are not disposable. In some embodiments, the first and second plurality of electrodes are mounted in a head that is configured to rotate to facilitate contact between the first and second plurality of electrodes and skin of the patient. In some embodiments, the TENS is configured to output a plurality of spaced biphasic electrical pulses including a plurality of pairs of pulses, each pair of pulses including a first pulse of a first polarity separated by a gap in time from a second pulse having a second polarity, opposite the first polarity. In some embodiments, the TENS is configured to output a plurality of alternating spaced biphasic electrical pulses including a plurality of pairs of pairs of pulses, each pair of pairs of pulses including a first pair having a first pulse of a first polarity separated by a gap in time from a second pulse having a second polarity, opposite the first polarity, followed by a longer gap in time by a second pair having a third pulse of the second polarity separated by a gap in time from a fourth pulse having the first polarity. In some embodiments, the TENS is configured to output a plurality of electrical, substantially square, alternating-spaced-biphasic pulses including a first plurality of pulses having a first polarity and a duration of no more than 200 microseconds and a second plurality of pulses having a second polarity, opposite the first polarity, and a duration of no more than 200 microseconds.

In some embodiments, the present invention provides an apparatus for treating a headache of a patient, the apparatus including a portable, transcutaneous electrical nerve stimulator (TENS) having a plurality of electrodes, wherein the TENS transcutaneously presents a plurality of electrical pulses to nerves of the patient, in order to treat headache pain.

In some embodiments, the TENS unit and the plurality of electrodes are housed in a unitary device, wherein the device has no exposed wiring, and wherein the device facilitates a self-administered treatment by the patient. In some embodiments, the TENS is configured to treat headache pain in an abortive manner. In other embodiments, the TENS is configured to treat headache pain in a preventive manner.

In some embodiments, the TENS is a handheld device. In other embodiments, the TENS is a hands-free device.

In some embodiments, a first plurality of electrodes is at a distance from a second plurality of electrodes, and the first plurality and the second plurality are each configured such that at least two electrodes touch the patient's skin simultaneously.

In some embodiments, the TENS delivers pulses at one or more frequencies between about 40 Hz and about 10 kHz. In some embodiments, the plurality of electrical pulses are delivered at no more than 30 mA, and in some embodiments, electrical pulses are delivered at no more than 60 mA. In some embodiments, each one of the plurality of electrical pulses is delivered at no more than 200 volts. In some embodiments, a pulse width of each one of the plurality of electrical pulses is equal or less than 400 microseconds.

In some embodiments, the plurality of electrical pulses stimulate at least one of the following nerve structures: the right and/or left greater occipital nerve(s), the right and/or left least (third) occipital nerve(s), the right and/or left lesser occipital nerve(s), the right and/or left great auricular nerve(s).

In some embodiments, the apparatus further includes a conductive gel applicator that selectively dispenses gel from a reservoir within the handheld device. In some embodiments, the apparatus further includes one or more delivery channels built into at least one of the plurality of electrodes and operatively connected to the reservoir.

In some embodiments, each one of the plurality of the electrodes are shaped and configured such that the plurality of electrodes facilitate contact between the plurality of electrodes and skin of the patient in bodily locations where hair impedes such contact. In some embodiments, each one of the plurality of electrodes has a comb-tooth shape to ensure that hair is combed out of the way as the patient moves the plurality of electrodes over the skin.

In some embodiments, the apparatus further includes a battery electrically connected to the TENS and housed within the unitary device. In other embodiments, the apparatus further includes an external power supply electrically connected to the TENS.

In some embodiments, each one of the plurality of electrodes is mounted in a device head that is configured to rotate to facilitate contact between the plurality of electrodes and skin of the patient.

In other embodiments, any combination of the above-described features is implemented.

References cited—the following Patents and Applications relate to the invention and all are incorporated herein by reference: U.S. Pat. No. 6,735,475, U.S. Pat. No. 5,078,928, U.S. Pat. No. 4,856,526, U.S. Pat. No. 4,627,438, and U.S. Patent Application Publication 2006/0173510.

Other references are as follows:

1. AHMED, H. E., P. F. WHITE, W. F. CRAIG, M. A. HAMZA, E. S. GHONAME & N. M. GAJRAJ; 2000; *Use of percutaneous electrical nerve stimulation (PENS) in the short-term management of headache*; Headache 40: 311-315.
2. BARTSCH, T. & P. J. GOADSBY; 2002; *Stimulation of the greater occipital nerve induces increased central excitability of dural afferent input*; Brain 125: 1496-1509.
3. BUCHGREITZ, L., A. C. LYNGBERG, L. BENDTSEN & R. JENSEN; 2007; *Increased prevalence of tension-type headache over a 12-year period is related to increased pain sensitivity. A population study*; Cephalalgia 27: 145-152.
4. CAROLEI, A., I. CIANCARELLI, D. CERONE & S. SACCO; 2003; *Comorbidities of migraine: a user-friendly overview*; The Journal of Headache and Pain; 4: s23-s25.
5. DARTIGUES, J. F., P. MICHEL & P. HENRY; 2003; *Evaluating the economic costs of migraine: interest of a comparative approach*; The Journal of Headache and Pain; 4: s63-s66.
6. JENSEN, R.; 2001; *Mechanisms of tension-type headache*; Cephalalgia 21: 786-789.
7. JENSEN, R.; 2003; *Peripheral and central mechanisms in tension-type headache: an update*; Cephalalgia 23 Suppl 1: 49-52.
8. MARTELLETTI, P. & M. LEONARDI; 2003; *The global impact of migraine*; The Journal of Headache and Pain 4: s1-s2.
9. MORK, H., M. ASHINA, L. BENDTSEN, J. OLESEN & R. JENSEN; 2004; *Possible mechanisms of pain perception in patients with episodic tension-type headache. A new experimental model of myofascial pain*; Cephalalgia 24: 466-475.
10. POPENEY, C. A. & K. M. ALO; 2003; *Peripheral neurostimulation for the treatment of chronic, disabling transformed migraine*; Headache 43: 369-375.
11. LIPTON, R. B., M. E. BIGAL, A. I. SCHER & W. F. STEWART; 2003; *The global burden of migraine*; The Journal of Headache and Pain 4: s3-s11.
12. RODRIGO-ROYO, M. D., J. M. AZCONA, J. QUERO, M. C. LORENTE, P. ACIN & J. AZCONA; 2005; *Peripheral Neurostimulation in the Management of Cervicogenic Headache: Four Case Reports*; Neuromodulation 8: 241-248.
13. SCHWEDT, T. J., D. W. DODICK, T. L. TRENTMAN & R. S. ZIMMERMAN; 2007; *Response to occipital nerve block is not useful in predicting efficacy of occipital nerve stimulation*; Cephalalgia 27: 271-274.

14. SOLOMON, S., P. KARFUNKEL & K. M. GUGLIELMO; 1985; *Migraine-cluster headache syndrome*; Headache 25: 236-239.
15. IANNAZZO, S., M. S. CATTARUZZA, S. DE FILIPPIS, F. ROSSI, E. PERATA, S. DI ROLLO, G. COLOPRISCO & P. MARTELLETTI; 2003; *Analgesic therapy for headache: consumption, appropriateness and costs*; The Journal of Headache and Pain 4: s84-s87.
16. STOVNER, L., K. HAGEN, R. JENSEN, Z. KATSARAVA, R. LIPTON, A. SCHER, T. STEINER & J. A. ZWART; 2007; *The global burden of headache: a documentation of headache prevalence and disability worldwide*; Cephalalgia 27: 193-210.
17. TERZI, T., B. KARAKURUM, S. LER, L. E.-NAN & C. TULUNAY; 2002; *Greater occipital nerve blockade in migraine, tension-type headache and cervicogenic headache*; The Journal of Headache and Pain 3: 137-141.
18. VINDING, G. R., P. ZEEBERG, A. LYNGBERG, R. T. NIELSEN & R. JENSEN; 2007; *The burden of headache in a patient population from a specialized headache centre*; Cephalalgia 27: 263-270.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A method for treating a headache of a patient, the method comprising:
    providing a portable head-band-mounted, transcutaneous electrical nerve stimulator (TENS) having:
        a first electrode set having a plurality of non-invasive comb-like electrodes physically connected to a common electrode base and each electrically connected to a first signal output of the TENS,
        a second electrode set having one or more non-invasive comb-like electrodes physically connected to the common electrode base, wherein the first electrode set and the second electrode set are configured to be simultaneously placed in contact with the patient's head, and wherein the second electrode set is electrically connected to a second signal output of the TENS, and
        a headband-type assembly that, after it has been placed on the patient's head, provides hands-free operation that does not require further handling and secures the first electrode set and the second electrode set against the patient's head, such that the first electrode set is held against a first elongated posterior area of the patient's head, and the second electrode set is held against a second elongated posterior area of the patient's head, wherein the first area and the second area are in a cranial-caudal relationship to one another;
    supporting, using the headband-type assembly, the headband-mounted TENS on the patient's head such that the patient is free to move while stimulation is being applied;
    receiving, by the TENS, an activation indication; and
    based on the activation indication, providing a plurality of electrical pulses between the first signal output of the TENS and the second signal output of the TENS such that the electrical pulses are applied between the first area and the second area in a vertical caudal-cranial direction transcutaneously to the patient's head, wherein the plurality of electrical pulses are configured to be charge-balancing and short enough in duration to stimulate nerves of the patient while minimizing stimulation of muscle contraction, in order to treat headache pain.

2. The method of claim 1, wherein the providing of the plurality of electrical pulses includes providing biphasic pairs of substantially square pulses, each pair of pulses including a first pulse having a first polarity and a duration of between about 50 microseconds and about 400 microseconds and, after a first gap-in-time delay of between about 50 microseconds and about 100 microseconds, a second, following, pulse having a second polarity, opposite the first polarity, and a duration of between about 50 microseconds and about 400 microseconds, and a second gap-in-time delay that is longer than the combined duration of the first pulse, first gap-in-time delay and second pulse.

3. The method of claim 2, wherein the providing of the TENS includes housing the TENS and the first and second electrode set in a unitary device that has no external wires, and wherein the unitary device facilitates a self-administered treatment by the patient.

4. The method of claim 2, wherein the providing of the plurality of electrical pulses treats headache pain in an abortive manner.

5. The method of claim 2, wherein the providing of the plurality of electrical pulses treats headache pain in a preventive manner.

6. The method of claim 2, wherein the electrodes of the first electrode set are grouped into a first group, wherein the electrodes of the second electrode set are grouped into a second group, wherein the first group is located at a distance from the second group that is greater than a distance between any two adjacent electrodes in each group.

7. The method of claim 2, wherein the first pulse has a duration of about 100 microseconds and, after the first gap-in-time delay of about 75 microseconds, the second pulse has a duration of about 100 microseconds.

8. The method of claim 2, wherein the first and second electrode set are mounted in a device head, the method further comprising disabling power to the first and second electrode set plurality of electrodes if no pressure is applied to the device head, and enabling pulsed power to the first and second electrode set if pressure is applied.

9. The method of claim 2, wherein each one of the first and second electrode set is hollow, and wherein the first and second electrode set are mounted in a device head, the method further comprising:
    dispensing a conductive gel through each one of the first and second electrode set of hollow electrodes; and
    disabling power to each one of the first and second electrode set of hollow electrodes if no pressure is applied to the device head.

10. The method of claim 1, wherein the providing of the plurality of electrical pulses includes stimulating one or more of the nerve structures selected from the group consisting of the right greater occipital nerve, the left greater occipital nerve, the right least (third) occipital nerve, the left least (third) occipital nerve, the right lesser occipital nerve, the left lesser occipital nerve, the right great auricular nerve, and the left great auricular nerve.

11. The method of claim 1, wherein the providing of the plurality of electrical pulses includes providing unspaced biphasic pairs of pulses, each pair of pulses including a first pulse having a first polarity and a duration of between about 50 microseconds and about 400 microseconds and a second, immediately following, pulse having a second polarity, opposite the first polarity, and a duration of between about 50 microseconds and about 400 microseconds and then a gap-in-time delay such that the pulse repetition rate is between about 200 Hz and about 1000 Hz.

12. The method of claim 1, wherein the second electrode set includes a plurality of electrodes.

13. The method of claim 1, wherein the providing of the plurality of electrical pulses includes providing pairs of biphasic electrical pulses, each pair of biphasic electrical pulses including a first pulse of a first polarity and a second pulse of a second opposite polarity and a zero voltage during a first gap-in-time delay of between about 50 microseconds and about 100 microseconds between the first pulse having the first polarity and the second pulse having the second polarity, opposite the first polarity, and then a zero voltage during a second gap-in-time delay immediately following the second pulse that is longer than the combined duration of the first pulse, first gap-in-time delay and second pulse.

14. An apparatus for treating a headache of a patient, the apparatus comprising:
   a portable head-band-mounted, transcutaneous electrical nerve stimulator (TENS) having a common electrode base;
   a first electrode set having a plurality of non-invasive comb-like electrodes physically connected to the common electrode base and each electrically connected to a first signal output of the TENS,
   a second electrode set having one or more non-invasive comb-like electrodes physically connected to the common electrode base, wherein the first electrode set and the second electrode set are configured to be simultaneously placed in contact with the patient's head, and wherein the second electrode set is electrically connected to a second signal output of the TENS, and
   a headband-type assembly that, after it has been placed on the patient's head, supports the head-band-mounted TENS on the patient's head such that the patient is free to move while stimulation is being applied, provides hands-free operation that does not require further handling, and secures the first electrode set and the second electrode set against the patient's head, such that the first electrode set is held against a first elongated posterior area of the patient's head, and the second electrode set is held against a second elongated posterior area of the patient's head, wherein the first area and the second area are in a cranial-caudal relationship to one another,
   wherein the TENS presents a plurality of electrical pulses between the first signal output of the TENS and the second signal output of the TENS such that the electrical pulses are applied between the first area and the second area in a vertical caudal-cranial direction transcutaneously to the patient's head, wherein the pulses are configured to be charge-balancing and short enough in duration to stimulate nerves of the patient while minimizing stimulation of muscle contraction, in order to treat headache pain.

15. The apparatus of claim 14, wherein the TENS includes a circuit configured to output the plurality of electrical pulses as a series of biphasic pairs of substantially square pulses, each pair of pulses including a first pulse having a first polarity and a duration of between about 50 microseconds and about 400 microseconds and, after a gap-in-time delay of between about 50 microseconds and about 100 microseconds, a second, following, pulse having a second polarity, opposite the first polarity, and a duration of between about 50 microseconds and about 400 microseconds.

16. The apparatus of claim 15, wherein the TENS unit and the first and second electrode set are housed in a unitary device, wherein the unitary device has no exposed wiring, and wherein the unitary device facilitates a self-administered treatment by the patient.

17. The apparatus of claim 15, wherein the electrodes of the first electrode set are grouped into a first group, wherein the electrodes of the second electrode set are grouped into a second group, wherein the first group and the second group are located at a distance from one another that is greater than a distance between any two adjacent electrodes in each group.

18. The apparatus of claim 15, further comprising a conductive gel applicator that selectively dispenses gel from a reservoir within the apparatus.

19. The apparatus of claim 18, further comprising one or more gel-delivery channels built into at least one of the second electrode set and operatively connected to the reservoir.

20. The apparatus of claim 15, wherein the first and second electrode set are shaped and configured to facilitate contact between the first and second electrode set and skin of the patient in bodily locations where hair would otherwise impede such contact.

21. The apparatus of claim 15, wherein each one of the first and second electrode set has a comb-tooth shape to ensure that hair is combed out of the way as the patient moves the plurality of electrodes over the skin.

22. The apparatus of claim 15, wherein the apparatus is small enough that a person can carry it around comfortably.

23. The apparatus of claim 14, wherein the TENS includes a circuit configured to output a plurality of electrical biphasic pulses, each pair of pulses including a first pulse having a first polarity and a duration of between about 50 microseconds and about 400 microseconds and, after a first gap-in-time delay of between about 50 microseconds and about 100 microseconds, a second, following, pulse having a second polarity, opposite the first polarity, and a duration of between about 50 microseconds and about 400 microseconds, and then a second gap-in-time delay that is longer than the combined duration of the first pulse, first gap-in-time delay and second pulse.

24. The apparatus of claim 14, wherein the second electrode set includes a plurality of electrodes.

25. The apparatus of claim 14, wherein the TENS includes a circuit configured to output the plurality of electrical pulses as a series of biphasic pairs of pulses, each pair of pulses including a first pulse having a first polarity and a duration of and about 100 microseconds, a second pulse having a second polarity, opposite the first polarity, and a duration of about 100 microseconds, and a zero voltage during a gap-in-time delay of about 75 microseconds between the first pulse and the second pulse.

26. The apparatus of claim 14, wherein the TENS includes a circuit configured to output the plurality of electrical pulses as a series of biphasic pairs of pulses, each pair of pulses including a first pulse having a first polarity and a duration of between about 50 microseconds and about 400 microseconds and, after a gap-in-time delay of between about 50 microseconds and about 100 microseconds, a second, following, pulse having a second polarity, opposite the first polarity, and a duration of between about 50 microseconds and about 400 microseconds.

27. An apparatus for treating a headache of a patient, the apparatus comprising:
   a portable head-band-mounted, transcutaneous electrical nerve stimulator (TENS) having:
      a first electrode set having a plurality of non-invasive comb-like electrodes physically connected to a common electrode base and each electrically connected to a first signal output of the TENS,
      a second electrode set having one or more non-invasive comb-like electrodes physically connected to the common electrode base, wherein the first electrode set and the second electrode set are configured to be simultaneously placed in contact with the patient's head, and wherein the second electrode set is electrically connected to a second signal output of the TENS, and
      a headband-type assembly that, after it has been placed on the patient's head, provides hands-free operation that secures the first electrode set and the second electrode set against the patient's head, such that the first electrode set is held against a first elongated posterior area of the patient's head, and the second electrode set is held against a second elongated posterior area of the patient's head, wherein the first area and the second area are in a cranial-caudal relationship to one another;
   means for supporting, using the headband-type assembly, the head-band-mounted TENS on the patient's head such that the patient is free to move while stimulation is being applied;
   means for receiving, by the TENS, an activation indication; and
   means, based on the activation indication, for providing a plurality of electrical pulses between the first signal output of the TENS and the second signal output of the TENS such that the electrical pulses are charge-balancing and are short enough in duration, when applied between the first area and the second area in a vertical caudal-cranial direction transcutaneously to the patient head, to stimulate nerves of the patient while minimizing stimulation of muscle contraction, in order to treat headache pain.

28. The apparatus of claim 27, wherein the second electrode set includes a plurality of electrodes.

* * * * *